United States Patent [19]
Nickel

[11] Patent Number: 5,780,242
[45] Date of Patent: Jul. 14, 1998

[54] BIOASSAY FOR THE SCREENING OF ION CHANNEL ACTIVE MOLECULES

[76] Inventor: Alfred A. Nickel, 1844 San Miguel, Walnut Creek, Calif. 94596

[21] Appl. No.: 356,388

[22] PCT Filed: Jun. 18, 1993

[86] PCT No.: PCT/US93/05792

§ 371 Date: Feb. 17, 1995

§ 102(e) Date: Feb. 17, 1995

[87] PCT Pub. No.: WO94/00748

PCT Pub. Date: Jan. 6, 1994

[51] Int. Cl.[6] .................... G01N 21/19; G01N 33/566; A61K 41/00; A61K 47/48
[52] U.S. Cl. .................... 435/7.2; 435/7.1; 514/1
[58] Field of Search .................... 435/7.1, 7.2; 514/1

[56] References Cited

FOREIGN PATENT DOCUMENTS 279757  8/1988  European Pat. Off. .

OTHER PUBLICATIONS

Butterworth IV, J.F. et al. "Mechanisms of Local Anesthesia: A Review". *Anesthesiology* 72(4):711–734 (1990).

Manavalan, P. et al. "Circular dichroism studies of acetylcholinesterase conformation. Comparison of the 11S and 5.6S species and the difference induced by inhibitory ligands". *Biochimica Et Biophysica Acta* 829(3):365–370 (1985).

Loret, E.P. et al. "An Anti–Insect Toxin Purified from the Scorpion *Ancroctonus autralis* Hector Also Acts on the α– and β–Sites of the Mammalian Sodium Channel: Sequence and Circular Dichroism Study". *Biochemistry* 30:633–640 (1991).

Pennington, M.W. et al. "Synthesis and Biological Activity of Six Monosubstituted Analogs of a Sea Anemone Polypeptide Neurotoxin". *Peptide Research* 3(5):228–231 (1990).

Wu, C.S et al. "Conformation of Acetylcholine Receptor in the Presence of Agonists and Antagonists". *Journal of Protein Chemistry* 9(1):119–126 (1990).

Darbon, H. et al. "Alpha–Scorpion neurotoxin derivatives suitable as potential markers of sodium channels". *International Journal of Peptide and Protein Research* 22(2):179–186 (1983).

Freschi, J.E. et al. "Effect of gamma radiation on sodium channels in different conformation in neuroblastoma cells". *Biochimica Et Biophysica Acta* 858(1):31–37 (1986).

Kitz, R.J. et al. "Conformational Changes of Acetylcholinesterase". *Molecular Pharmacology* 4(1):104–107 (1968).

*Primary Examiner*—Ponnathapura Achutamurthy
*Attorney, Agent, or Firm*—Albert P. Haullin; Howrey & Simon

[57] ABSTRACT

Thus invention relates generally to a bioassay technique to measure the interaction of molecules with ion channels and in particular, sodium channels. More specifically, the present invention relates to the use of circular dichroism to diagnose ion channel, I. e., potassium, calcium and preferably sodium channel disease or dysfunction and a method for screening ion channel active molecules. This invention further provides a novel means to treat cancer associated with diseased dysfunction of ion channels, and especially sodium channel thermal proteins.

10 Claims, 3 Drawing Sheets

BIOASSAY FOR THE SCREENING OF ION CHANNEL ACTIVE MOLECULES

FIELD OF THE INVENTION

This invention relates generally to a bioassay technique to measure the interaction of molecules with ion channels and in particular, sodium channels. More specifically, the present invention relates to the use of circular dichroism to diagnose ion channel, i.e., potassium, calcium and preferably sodium channel disease or dysfunction and a method for screening ion channel active molecules. This invention further provides a novel means to treat cancer associated with diseased dysfunction of ion channels, and especially sodium channel thermal proteins.

BACKGROUND OF THE INVENTION

The ion channel, especially the sodium channel is a transmembrane protein responsible for the voltage-dependent modulation of the sodium ion permeability of excitable membranes and thus plays an essential role in generating action potentials. Hille, B., *Ionic Channels of Excitable Membranes*, Sinauer, Sunderland, Mass. (1984). Propagation of the action potential in nerve and muscle cells is generally thought to occur by transient changes in the permeability of the cell membrane to $Na^+$, $K^+$ or $Ca^{++}$ ions via a specific channel. Two events can be distinguished in the passage of $Na^+$, $K^+$ or $Ca^{++}$ through the channel: 1) selective filtering and 2) rapid increase in the permeability to $Na^+$, $K^+$ or $Ca^{++}$ by a gating type of mechanism. Angelides, K. J. and T. J. Nuttov, *J. Biol. Chem.* 258:11858–11867 (1981). In addition, ion channels may be either voltage gated (e.g., $Na^+$ and $Ca_{2+}$ channels) implying that current is gated (or regulated) by membrane potential (voltage), or chemically gated (e.g., acetylcholine receptors and γ-aminobutyric acid receptors) implying that current is gated primarily by binding of a chemical rather than by the membrane potential. Butterworth, J. F. and G. R. Strichartz, *Anesthesiology* 72:711–734 (1980).

Sodium channels have been isolated and purified by biochemical methods. See, Merksey, B. D., U.S. Pat. No. 4,895,807 (1990). Recently, sodium channels from the electric organ of the eel and rat brain have been cloned and sequenced. Kayano, et al. *FEBS LETTERS* 28: 181–184 (1988). The amino acid sequences of the $Na^+$ channel found in eel electroplax has been deduced from its gene sequence. From this deduction, Kayano, et al. propose that the channel has large hydrophobic regions, probably in α-helical conformations that span the membrane, interspersed with hydrophilic regions to form a Na+ ion conducting "pore" of the channel. It is believed that the α-helical structures provide conformational flexibility for the sodium channel which is functionally responsible for the channels "open" and "close" gating mechanism. Oiki, et al., *Proteins*, 8:226–236 (1990).

The pharmacology of sodium channels has been extensively studied. A variety of protein and nonprotein toxins are found to modify the physiology of $Na^+$ channels. At present, six different binding sites for toxins have been postulated. These include extracellular surface sites for tetrodotoxin and for two different classes of peptide toxins (αand β, usually isolated from scorpion venoms), intramembranous sites for three classes of lipophilic organic molecules (brevetoxin/ciguatoxin and the classical activators such as batrachotoxin and veratridine, and certain synthetic insecticides), and the site(s) of local anesthetics action. Each of these sites appear to be linked to at least one other site via conformationally coupled interactions that often are dependent on the membrane potential. Butterworth, J. T. and G. R. Strichartz, *Anesthesiology*, 72:711–734 (1990).

Many diseases of excitable tissues are known to be associated with, if not caused by, dysfunction of ion channels; these include cardiac arrhythmias, angina pectoris, cystic fibrosis, myotonia, and epilepsies, to mention only a few. A variety of drugs, for example, local anesthetics, antiarrhythmic agents, anticoconvulsants and psychoactive drugs, have been developed to treat these diseases. Channel dysfunction can now be studied due to theoretical and technological developments in this area. A better understanding of the channel mechanism may potentially lead to the discovery of more novel molecules possessing greater therapeutic effects on these diseases.

More recently, sodium channel dysfunction has been linked to the formation of cancer. Certain cancers are clinically diagnosed solely on their neurological symptoms before the actual tumors can be located due to their capabilities to make clinically important neuropeptides. Therefore, study of the sodium channel may not only provide potential solutions to diseases directly associated with the dysfunction of the channels, it may also provide information on the early formation of tumors.

Several techniques have been developed to evaluate the gating mechanism of the sodium channel and the mode of action of channel-drug interaction. Electrophysiological recording has been used to define the roles of $Na^+$ ana $K^+$ currents in generating action potentials in excised nerves. Hodgkin, A. L. and A. F. Huxley, *J Phiol*: 116:473–486 (1952). This technique, however, is not suitable for mass screening of compounds due to its technical complexity and the requirement of a high degree of sophistication to produce reproducible results. Recently, radioligand binding assays have been employed to characterize the site of action of various classes of sodium channel blockers. However, the availability of radiolabelled ligands, the level of nonspecific binding, and the physico-chemical property of the molecules may limit the application of this technique. Strichartz, et al., *Ann. Rev. Neurosci* 10:239–67 (1987). Fluorescent-labelled neurotoxin probes have also been used to map the molecular structure of the functional site of the channel, but have not gained general popularity for broader use. Angelides, K. A. and T. J. Nuttov, *J. Biol. Chem.* 256:11958–11967 (1983) Consequently, there exists an apparent need for an alternative technique which may enable the large scale screening of molecules involved in the sodium channel in a simple and reliable manner.

Application of circular dichroism to solutions of macro-molecules has resulted in the ability to identify conformational states of these macromolecules. The technique can distinguish random coil, alpha helix and beta chain conformation states of macromolecules and therefore is a unique tool for the characterization of the secondary structure of membrane bound enzymes such as acetylcholine esterase (AchE). Nickel, A. A., *Master Thesis*, University of California, San Francisco - 72 pp. (1968) (Unpublished.). Additionally, circular dichroism has been used to characterize the intra-molecular conformational change of various polypeptide neurotoxins such as scorpion and sea anemone neurotoxins. Loret, et al., *Biochemistry* 30: 633–640. Mahnir, V. M. and E. P. Kozlovosaya, *Texicon* 28: 818–826 (1981). More importantly, the secondary structure of the α-peptide of rat brain sodium channels has also been elucidated by circular dichroism. The result shows that the α-peptide is a conformationally flexible polypeptide that contains mostly β-sheet and random coil which fold into a conformation consisting of approximately 65% α-helix. Elmer, et al., *Biochemistry* 24: 8128-8137 (1988), Oiki, et al., *Proteins* 8:226-236 (1990). The Elmer, et al. finding is consistent with the earlier hypothesis that the α-peptide is functionally related to the gating mechanism of sodium channels.

Paresthesia can be defined as an altered sensation of numbness, burning or prickling that may reflect an alteration in the sensation of pain in the distribution of a specific sensory nerve. Paresthesia is a rare clinical finding subsequent to oral surgery accompanied by the administration of local anesthetics. Patients who demonstrate such symptoms after surgery frequently suffer neurotoxicity which may be explained by the interaction of anesthetic metabolites with a specific neuroreceptor that is presumably responsible for the transmission of sensory nerve impulse.

Although it is well established that misuse of local anesthetic may cause paresthesia which, as described above, presumably results from the interaction of a reactive metabolite derived from local anesthetics with the α-helix conformation of the sodium channels. Nickel, A. A., *Aneth Prog.* 37:42-45 (1990). Very few studies have been conducted to elucidate the real mechanism of the neurotoxicity. Consequently, a means of reducing or avoiding paresthesia remains an important research subject for clinical use of local anesthetics.

Based on the studies of paresthesia injuries to oral surgery patients, it is now believed by the present inventor that it is theoretically possible that those patients with an apparently "wrong" conformation in their ion channel, especially the sodium channels, are no longer capable of conducting nerve impulse. One plausible reason for this incapacity is due to the "sticking" of a reactive anesthetic metabolite within the "pore" of the sodium channels thus prevent the normal functioning of the channels and the transport of the ions.

Local anesthetics are a class of similar chemicals that reversibly block the peripheral and central nerve pathways following regional administration. The actual site of local anesthetic molecular action is the sodium channel membrane pore which regulates ion influx. The neuroreceptor site in the pore must have the ability to undergo conformational change from a closed to an open configuration to accommodate rapid changes in membrane potential. Local anesthetics are further classified as short, moderate or long acting agents depending on their capability and duration in time to block the sodium channels.

In view of the complexity of ion channel pharmacology, especially sodium ion channel pharmacology and its attractiveness as a target site for the discovery and design of novel therapeutic or agricultural compounds, there is, therefore, an apparent need for a simple and alternative bioassay that would allow diagnosis of the abnormality of sodium channels as well as the screening of potentially sodium channel active molecules in a rapid and reliable manner. The present invention, by the use of circular dichroism, provides such an alternative.

SUMMARY OF THE INVENTION

The present invention provides a novel means to screen ion channel, i.e., potassium, calcium or sodium channel active compounds using circular dichroism by employing a method of comparing a test compound that can stabilize the helical transition of the ion channel of a thermal protein from a coiled conformation to an uncoiled conformation at different temperatures ranging from 25°–50° C. in the presence of a thermal protein. Such method provides a unique characteristic for the screening of molecules capable of interacting with ion channels, such as potassium, calcium or sodium channel thermal proteins Another aspect of the present invention relates to a method to diagnose ion channel abnormality of a patient or an animal by comparing the characteristic of their ion, preferably the sodium channel thermal protein between diseased and healthy excitable tissues of the patient or animal using circular dichroism.

Another unique aspect of the present invention is directed to a novel method for determining abnormality in the structural function of a thermal protein that possesses ion or sodium channel functionality. Specifically, the method comprises the steps of: (a) forming a mixture of a thermal protein and a molecule capable of blocking or preventing the normal function of the ion, preferably the sodium channel in an excitable cell; (b) subjecting the mixture to circular dichroism at a wave length of 222 nM, measuring the transition of molar ellipticity of the mixture at two or more temperatures of said mixture ranging between 25°–50° C., and (c) comparing said transition of molar ellipticity with the transition of molar ellipticity of a controlled thermal protein. Preferably the temperatures of the mixture are adjusted at 30° and 35° C., i.e., data is taken at these two temperatures, because these are the temperatures that local anesthetics exert their greatest activity in circular dichroism from which strong differences in measurements can be recognized, as shown in the data below and in FIG. 2.

Another aspect of the present invention relates to a method of treating cancer associated with disease or dysfunction of ion channel thermal proteins, i.e., potassium, calcium or sodium, preferably sodium channel thermal proteins. This aspect of the invention involves the theoretical affinity of lidocaine and its derivatives for the ion channel. Specifically, the method involves modifying a molecular form of a non-carcinogenic lidocaine derivative (e.g., the long chain residue of the molecule is modified) to make it radiosensitive to ionizing radiation as a first step. Secondly, administering this modified ion channel-seeking drug (the modified lidocaine) in the mammal or patient and subjecting the mammal or patient to particle beam high energy radiation to activate the drug once it is in place in the ion channel. The radiation beam then selectively destroys cancer-associated dysfunctional channels and which leads to tumor resolution. The current ionizing radiation preferably has a 40 angstrom definition of specificity and the radiosensitive, ion, preferably sodium channel-seeking drug of the present invention is specific only to a 4 angstrom site of action which is the size of the ion channel structure itself. Thus, the present invention provides a new and selective means for treating cancer associated with dysfunction or disease of ion and especially sodium channel thermal proteins.

One more aspect of the present invention is directed to the diagnosis of diseases associated with the disease or dysfunction of ion channel thermal proteins by using the methods of the present invention. By use of the methods of the present invention the study of the disease or dysfunction can be accomplished, thus assisting researchers in the understanding of the disease or dysfunction, and means for seeking treatment and possible cures. Specifically, the test protein can be obtained from the excitable tissues derived from a diseased mammal and where said diseases are selected from the group consisting of CNS diseases, cardiac disease, peripheral nervous system disease, tumors, cardiac arrhythmias, angina pectoris, cystic fibrosis, myotonia and epilepsies.

Still another aspect of the invention relates to the measurement of the temperature-dependent conformational change of ion, especially sodium channel thermal proteins at 222 nM wavelength by circular dichroism. The sodium channel is known to regulate sodium ion conductance by changing its conformation in response to the change of membrane voltage and to the binding of channel active ligands. This method of the invention shows that a major helical transition occurs when the thermal protein is tested at temperatures between 30° C. and 35° C., and this transition can be blocked if the sodium channel is properly stabilized by sodium channel active molecules, such as lidocaine or derivatives thereof.

Consequently, another feature of the present invention relates to a method for determining when a compound is capable of blocking or impairing an ion channel such as the sodium channel. The method comprises: (a) forming a mixture of a thermal protein and a compound capable of blocking or preventing the normal function of the sodium channel in an excitable cell of a thermal protein and the test compound; (b) subjecting the mixture to circular dichroism at a wave length of 222 nM wave length and measuring the transition of molar ellipticity at different temperatures of said mixture ranging between 25°–50° C., and (c) comparing said transition of molar ellipticity with the transition of molar ellipticity of a controlled thermal protein alone and a mixture of the thermal protein and said compound capable of blocking or preventing the normal function of the sodium channel in an excitable cell.

As discussed above, one class of ion channel, especially the sodium channel molecules that are capable of stabilizing the ion channel thermal protein and thus preventing helical transition are the anesthetics. For example, lidocaine and lidocaine derivatives can prevent the observed helical transition between 30° C. to 35° C. and, consequently, is used as a model compound for the elucidation of ligand-channel interaction. Local anesthetics are further classified as long, intermediate and short term agents based on their potency. It is, therefore, likely that the present invention can be further developed to measure the relative affinities of binding of these local anesthetics to the sodium channel.

Preferred molecules capable of interacting and affecting the normal function of ion channel thermal proteins are selected from the group consisting of lidocaine, derivatives of lidocaine, and anesthetics having functions similar or the same as lidocaine.

Another series of compounds that are capable of forming a mixture with abnormal sodium channels and consequently block or prevent the functioning of the channels are generally characterized as sodium channel blockers. For example, these molecules have a binding site on sodium channels and said binding site is directly or indirectly linked with the binding site of the local anesthetic such as lidocaine. These molecules are selected from, but not limited to, the following categories of compounds: (a) tetrodotoxin and its derivatives that are capable of blocking the sodium currents; (b) batrachotoxin, veratridine and their lipophilic derivatives and analogs that are capable of activating sodium channels; (c) α-, or β-scorpion toxins, sea anemone polypeptide neurotoxins and their respective derivatives that are capable of prolonging the open status of sodium channels; (d) DDT and synthetic pyrethroid insecticides and their analogs that are capable of activating sodium channels; (e) compounds that are capable of blocking sodium channels in a manner different from tetrodotoxin and possess anticonvulsant and/or antiarrhythmic activity.

Likewise, compounds possessing antiarrhythmic or anticonvulsant activity may also prevent the characteristic helical transition of the sodium channels. Antiarrhythmic compounds are known to produce rapid block on cardiac sodium channels and, thus, prevent unwarranted cardiac muscle contractions. The anticonvulsant compounds are used to block sodium channel in the central nervous system and have been used to treat epilepsies and seizures. This invention provides a unique bioassay technique for measuring the interaction of these compounds with sodium channels.

DDT and synthetic pyrethroids are yet another class of compounds interacting with sodium channels. These compounds induce repetitive nerve firing in insect tissues and consequently cause excitatory contractions and convulsions in the poisoned insects. Synthetic pyrethroids are currently used as contact insecticides for the control of economically and agriculturally important insect pests. The present invention, by characterization the conformational status of sodium channel, can be used as a reliable tool to screen sodium channel active molecules with potential insecticidal activity.

DEFINITION OF TERMS

For the purpose of clarity, the following terms are defined and so used in the present invention:

(1) Circular dichroism (CD) is an absorptive phenomenon that results when a chromophore interacts with plane polarized light at a specific wavelength. The absorption band can be either negative or positive depending on the differential absorption of the right and left circularly polarized components for that chromophore. Unlike optical rotatory dispersion (ORD) that measures the contributions of background and the chromophore of interest many millimicrons from the region of actual light interaction, circular dichroism offers the advantage of measuring optical events at the wavelength at which the event takes place. Circular dichroism, then, is specific to the electronic transition of the chromophore. Beychok, S., *Science* 154: 1288–1289 (1966).

(2) Neuroreceptor—neuroreceptor is a macromolecule generally associated with the nervous system and has specific binding sites for the recognition of a series of ligands and the binding of said ligands to the macromolecule will induce a neurophysiological response.

(3) Molar ellipticity—molar ellipticity is an unit used by the present invention to express the transitional activity of a given conformation at a specific wavelength.

(4) Thermal protein—thermal proteins are macromolecular proteins that are capable of exhibiting a helix-coil transition at different elevated temperatures without increase or decrease in protein activity. Acetylcholinesterase ("AChE") is a typical thermal protein under this definition.

BRIEF DESCRIPTION OF THE DRAWINGS

The following is a brief description of the drawings. More detailed descriptions of the drawings are found in the Example section of this specification.

DETAILED DESCRIPTION OF THE INVENTION

Figure 1:
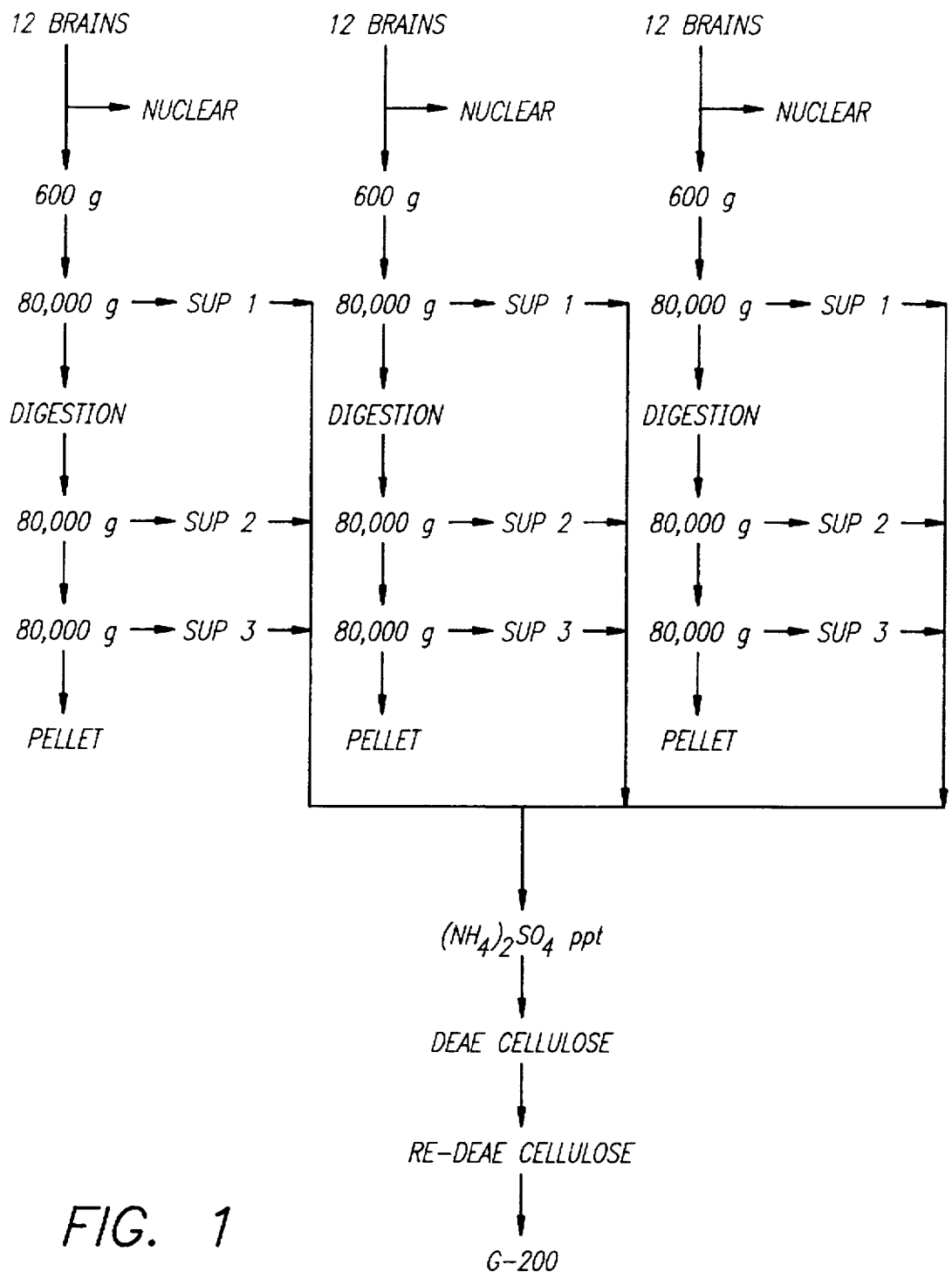
FIG. 1 is the outline of the experimental procedures for the preparation, isolation and purification of neuroreceptors from beef brains.

Biological protein macromolecules are made up of asymmetric monomer units, L-amino acids, so that they all possess the attribute of optical activity. Additionally, rigid structures like DNA or an alpha helical polypeptide have optical properties that can be measured using the appropriate spectroscopic system. In fact, large changes in an easily measured spectroscopic parameter can provide selective means to identify conformational states and changes in conformational states under various circumstances, and sometimes to observe the perturbation of single groups in or attached to the macromolecule.

Circular dichroism is a spectroscopic parameter capable of giving information about an individual optically-active absorption band at a wavelength specific for that chromophore (e.g., for example, an electron transition of a helix at 222 nm).

The Pasteur principle states that an optically active molecule must be asymmetric; that is, the molecule and its mirror image cannot be superimposed. Plane polarized light consists of a combination of left circularly polarized light and right circularly polarized light traveling in phase. The interaction of this light with an asymmetric molecule results in a preferential interaction of one circularly polarized component which, in an absorption region, will be seen as a differential absorption (i.e., a dichroism). Urry, D. W., *Spectroscopic Approaches to Biomolecular Conformation*, American Medical Association Press, Chicago, Ill., pp 33–120 (1969).

Circular dichroism, then, is an absorptive phenomenon that results when a chromophore interacts with plane polarized light at a specific wavelength. the absorption band can be either negative or positive depending on the differential absorption of the right and left circularly polarized components for that chromophore. Unlike optical rotatory dispersion (ORD) that measures the contributions of background and the chromophore of interest many millimicrons from the region of actual light interaction, CD offers the advantage of measuring optical events at the wavelength at which the event takes place. Circular dichroism, then, is specific to the electronic transition of the chromophore. Beychok, S. "Circular Dichroism of Biological Macromolecules", *Science*, 154:1288–1299 (1966).

Application of circular dichroism to solutions of macromolecules has resulted in the ability to identify conformation states (Jirgensons, B. *Optical Rotatory Dispersion of Proteins and Other Macromolecules*, Springer-Verlay, Berlin, Germany, pp. 20–39, 1969, and Gratzer, W. B. and Cowburn, D. A., "Optical Activity of Biopolymers", *Nature*, (see Beychok, supra) 222:426–431 (1969). The technique can distinguish random coil, alpha helix, and beta chain conformation states of macromolecules. In proteins, alpha helical fibrous proteins show absorption curves closely resembling those of alpha helical polypeptides, but in globular proteins of known structure, like lysozyme and ribonuclease, the helical structures are in rather poor agreement with X-ray cyrstalography work. A further source of difficulty in globular proteins is the prevalence of aromatic chromophores on the molecules around 280 nm. An interesting example of helical changes has been demonstrated using myoglobin and apomyoglobin. After removing the prosthetic group heme, the apoprotein remaining has a residual circular dichroic ellipticity reduced by 25%. This loss of helix is attributable to an uncoiling of 10–15 residues in the molecule. Other non-peptide, optically active chromophores include tyrosine, tryptophan, phenylalanine, and cystine when located in the primary amino acid sequence of a macromolecule. Examples of non-peptide ellipticities include the disulfide transition in ribonuclease and the cystine transitions of insulin (See Beychok, supra).

Characterized acetylcholinesterase has been isolated primarily from the ell, *Electrophorous electricus*. Attempts to purify this enzyme from mammalian brain tissue have resulted in limited success because of the strong enzyme-membrane association. Relatively severe biochemical techniques have been used to solubilize this enzyme. S. L. Chan has shown that a more gentle methodology using homogenization and centrifugation in 0.32 M sucrose containing 1 mM EDTA can solubilize the enzyme in a relatively pure form (Chan, S. L. et al., "Purification and Properties of Brain Acetylcholinesterase", Journal of Neurochemistry (1971)).

Interest in the acetylcholinesterase is a result of three factors. It may be involved in the cholinergic receptor mechanism of neuronal transmission. It is known to be a target site for drug action. Finally, it is believed to terminate the action of the neuronal transmitter (Burger, A. (ed.) *Drugs Affecting the Peripheral Nervous System*, Vol. 1, Marcel Dekker, Inc., New York, 1967, and Goodman, L. S. et al., *The Pharmacological Basis of Therapeutics*, MacMillan Co., New York, 1970).

Optical studies using eel acetylcholinesterase and ORD have suggested that heat, strong base, substrate, and anticholinesterase drugs affect the conformation of this enzyme (Kitz, R. J. et al., "Conformational Changes of Acetylcholinesterase", *Molecular Pharmacology*, 4:104–107, (1968)). Unfortunately, the published data present problems in terms of proper control data and spectrophotometric curves of questionable quality. These data were extrapolated to suggest that acetylcholinesterase was an allosteric enzyme (Chan, S. L. et al., supra). Allosterism, by definition, is the ability of molecular conformational changes to affect the rate of catalytic site action. Allosterism cannot be equated with the property of mechanical molecular movements necessary for function because this property may be divorced from catalytic activity.

Circular dichroism was selected for the purpose of the present invention as the method to examine ion channels, particularly sodium channels. Brain membrane isolated from mammalian brain tissue was used as the source of the thermal protein. Initially, the protein preparation was purified to a reasonable degree. Then, the spectrum of the preparation was determined using circular dichroism Since elevated temperatures often results in denaturation of the protein, it was felt that any gross conformational changes might be studied using the change in temperature as a probe of conformation. If significant changes occurred during denaturation, the influence of ion or sodium channel drugs possibly would shed light on the nature of the conformational changes.

Alpha helix at 222 nM is used to monitor the effect of temperature change on the ion channel's conformational change. In the absence of ion or sodium channel active molecules, a sharp helical transition occurs in the temperature region near that of the bovine body temperature of 38.5° C. When the membrane preparation is monitored between a broader temperature range such as from 15° C. to 60° C., a gradual, but irreversible and endothermic helix-coil transition is observed between 30° C. and 40° C. (See FIG. 2). Simultaneous measurement of AChE activity gave a temperature dependent curve with a maximum of 37° C.–41° C., however, the helix-coil occurred without significant increase or decrease in enzyme activity. In addition, enzyme activity is rapidly lost at 55° C. without a significant change in helix contact of the enzymes. It is suggested that the helix-coil transition observed between 30° C. to 40° C. is not due to the conformational change of AChE, but due to some other molecular component in the brain preparation that exhibits the observed helix-coil transition.

As the consequence of the technique of circular dichroism, one unique feature of the present invention is to use this technique to develop a method for determining abnormality in the structural function of a thermal protein that is associated with sodium ion or channel biochemical functionality. In addition, circular dichroism can also be used to identify molecules that interact specifically with ion or sodium channels. Consequently, another feature of the present invention relates to a method for determining when a compound is capable of blocking or impairing an ion channel of the thermal protein especially a sodium channel thermal protein.

Figure 2:
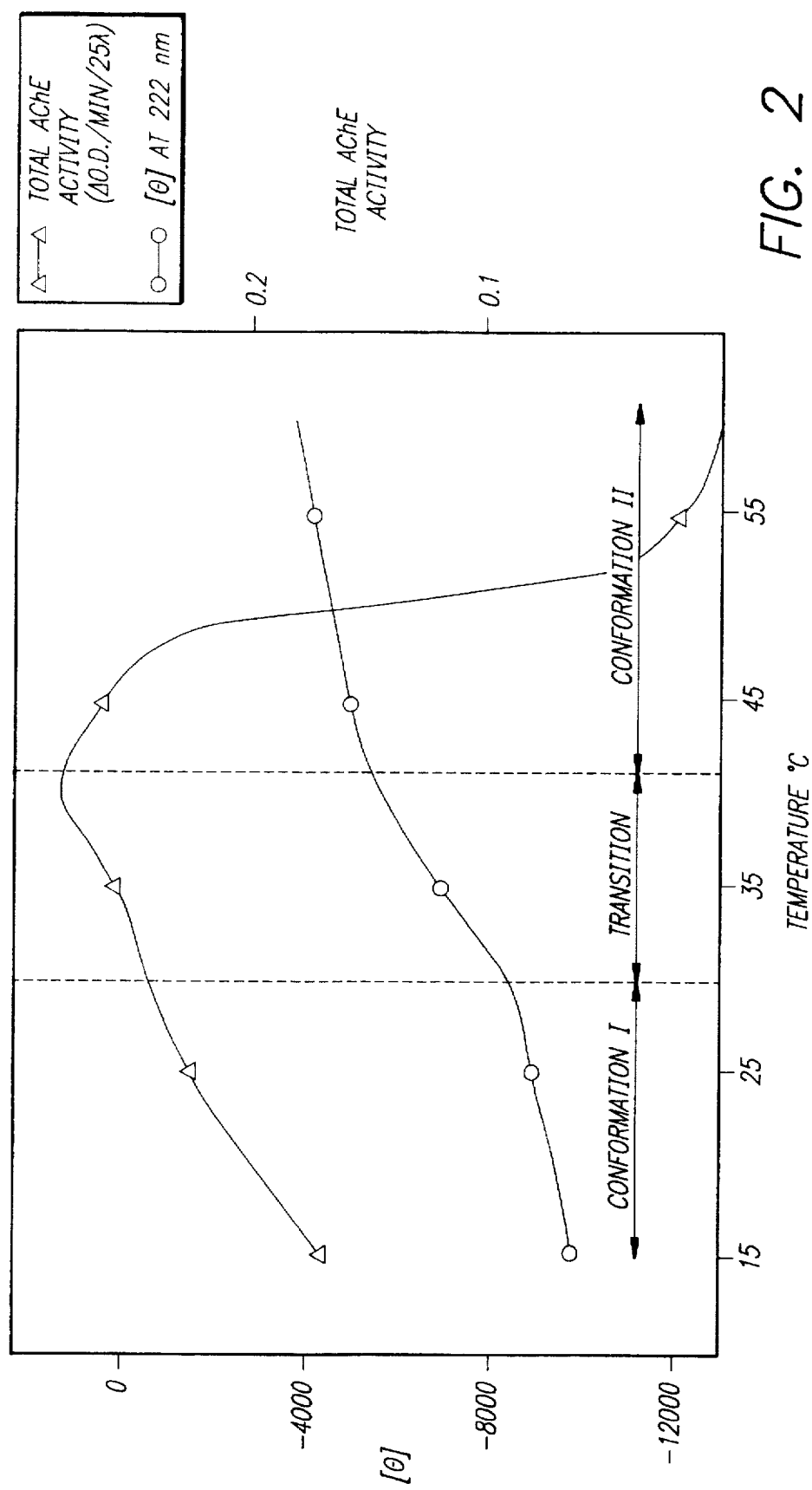
FIG. 2 presents the circular dichroism of sodium channel neuroreceptor at different temperature ranges. The activity of AChE is simultaneously measured to show that the helix-coil transition occurred without significant increase or decrease in enzyme activity.

More specifically, the method of the present invention comprises: (a) forming a mixture of a thermal protein and a compound capable of blocking or preventing the normal function of the ion channel preferably the sodium channel of the thermal protein in an excitable cell comprising a thermal protein and the test compound; (b) subjecting a mixture to circular dichroism at a wave length of 222 nM wave length measuring the transition of molar ellipticity while varying the temperature of said mixture between 25°–50° C., and (c) comparing said transition of molar ellipticity with the transition of molar ellipticity of a controlled thermal protein alone and a mixture of the protein and said compound capable of blocking or preventing the normal function of the sodium channel in an excitable cell. At least two and preferably three comparative data are taken at temperatures of 25° C. to 50° C. Most preferably, data are taken at 30° C., 35° C. and 40° C., for best results as shown in FIG. 2. By comparison of the data and curves generated, disease or dysfunction of the ion channel thermal protein can be determined by comparison with a normal test sample.

Local anesthetics and a series of neurotransmitter receptor agonists and antagonists have been known to interact with sodium channels. However, the effects of those sodium channel active molecules on the temperature-dependent helix transition have rarely been studied in circular dichroism. An unique feature of the present invention is directed to study the effects of lidocaine (i.e., a local anesthetic) and pilocarpine (i.e., an acetylcholine receptor agonist) on the helix-coil transition of beef brain preparation at 222 nM between 15° C. to 60° C. Surprisingly enough, the present invention shows that both lidocaine and pilocarpine can prevent the helical transition normally observed between 30°–35° C. in the absence of these compounds (see Example 3 for details) and stabilize the coiled helix in the most tightly coiled configuration. These compounds, therefore, seem to be able to stabilize the helix conformation of the sodium channel and to prevent the temperate-dependent uncoiling of alpha helix between 30° C.–35° C. When the temperature increases from 35° C. to 40° C., the alpha helix uncoils to equal the helix in the control sample. Consequently, the present invention provides a unique bioassay technique that allows the screening of ion, preferably sodium channel thermal protein active molecules with ion or sodium channel by temperature-dependent circular dichroism.

In addition to local anesthetic and various neurotransmitter receptor ligands, there are several classes of molecules, either naturally occurred or synthetically provided, bind to ion and preferably sodium channels exerting a wide spectrum of pharmacological activity. Butterworth, J. T. and G. R. Strichartz, Anesthesiology, 72:711–734 (1990). These molecules include, but are not limited to, protein toxins such as α-; β-scorpion toxin; sea anemone toxins; nonprotein toxins such as tetrodotoxin and its derivatives; lipophilic organic molecules such as brevetoxin, batrachotoxin, veratridine and synthetic insecticides, such as DDT and pyrethroids; and compounds possessed anticonvulsant and antiarrhythmic activity. Classically, local anesthetics have been known to link allosterically with most of the sodium channel binding sites that are the putative targets of these organic molecules or protein toxins, therefore, the present intention also provides an unique tool to screen molecules that have ion or sodium channel activity and are allosterically linked with the local anesthetic binding site.

Another unique feature of the present invention, is to use the method as a diagnostic tool to detect diseases associated with the disease or dysfunction of ion channel thermal proteins. These diseases include, but are not limited to, cardiac arrhythmias, angina pectoris, cystic fibrosis, myotonia and epilepsies, to mention only a few. The ion or sodium channels from diseased tissues can be isolated and purified and then tested by circular dichroism bioassays using the sodium channel thermal proteins prepared from a normal patient as a positive control. The difference in the circular dichroism spectrum can be used as an indicator to diagnose and predict such diseases.

Although ion channel thermal proteins including sodium channel thermal proteins have been genetically and biochemically purified by various researchers, Cherksey, B. P., U.S. patent application Ser. No. 4,895,807;

U.S. patent application Ser. No. 4,950,591, and International Patent Application PCT/US89/00558, the present invention is distinguishable from these disclosures because none of these disclosures relate to the use of circular dichroism as a bioassay technique to investigate the interaction of sodium channel molecules at 222 nM in a temperature-dependent manner. Moreover, none of these publications make such findings that local anesthetic drugs and neurotransmitter receptor ligands can stabilize an ion or the sodium channel specifically at 30° C.–35° C., i.e., when the alpha-helix is in the most coiled structure. The present invention, consequently, not only provides a unique aspect for the study of ion channel or sodium channel conformation, but also provides a tool to screen molecules that act on ion, and preferably sodium channels.

One more unique aspect of the present invention is related to the isolation and purification of ion channel thermal proteins and preferably sodium channel receptors suitable for circular dichroism described herein.

More specifically, the following examples give detailed description regarding the preparation, isolation and purification of beef brain sodium channels thermal proteins and the methodology of circular dichroism for the measurement of helical transition in the absence or presence of lidocaine and pilocarpine at 222 nM. It is noteworthy that brain membrane preparation, if not freshly prepared as described in Example 1, will not be protected by lidocaine or pilocarpine in the circular dichroisin assay. A detailed discussion related to this phenomena is shown below.

EXAMPLE 1

Preparation of Sodium Channel Protein with Mammalian Neuroreceptor

A. Dissection

Twelve beef brains are obtained from a local slaughter house (Chan, S. L. et al., supra). Brains freshly removed from the skull and still warm are used for brain membrane preparation. The brains are placed on ice and rushed to the laboratory, and immediately the caudate nuclei are removed. Dissection is done in situ by quickly removing the membrane and blood vessels located over the caudate with tweezers. Using a spatula, the caudate is carefully stripped away from the internal capsule, minimizing the presence of all white matter. The caudate head (up to the point where it intersects with the putamen of the lenticular nucleus) and the body and tail are removed. They are placed immediately on ice in a weighed beaker containing 50 ml of 0.32M sucrose (Mallinckrodt analytical reagent) with 1 mM EDTA, pH 6.9. [The entire dissection has to be completed in one hour after the brains are removed from the skull to minimize the effect of algor mortis usually occurring one and one half hours after death.]

B. Homogenization and Fractionation All steps of the purification are carried out in a cold room at 4 degrees centigrade. The caudates are cut up with scissors and homogenized mechanically with a Kontes dounce tissue grinder using pestle #A (large clearance). The homogenized caudates are suspended in 0.32M sucrose with 1 nM EDTA, pH 6.9, to give a 20% (w/v) homogenate in a volume of 250 ml. The suspension is then homogenized ten times at 3300 rpm in a Kontes Potter-Elvehjem tissue grinder.

The homogenate is centrifuged in the 9RA head of a Lourdes Model A2 Betafuge centrifuge at 600 g for 10 minutes at 0–4 degrees centigrade. The supernatant is removed and kept on ice. The pellet is resuspended in 250 ml total of 0.32M sucrose in 1 nM EDTA, pH 6.9, with five strokes of pestle #A in the Kontes dounce tissue grinder. The suspension is centrifuged in the 9RA head at 600 g for 10 minutes. The supernatant is removed and combined with the earlier supernatant to give the post 600 g fraction. The remaining nuclear pellet is discarded.

The post 600 g supernatant is then centrifuges in the FA-30 head of the Spinco Model L centrifuge for 75 minutes at 80,000 g. The supernatant remaining, termed supernatant 1, is assayed and discarded because of low AChE yield. (Note: AChE has been used as a marker enzyme for this study to monitor purification scheme for its catalytic activity associated with nerve system.) The pellets are then suspended with five strokes of a Kontes dounce tissue grinder with pestle #A in 250 ml of cold 0.32 sucrose in 1 mM EDTA, pH 6.9. The suspension is then stirred slowly overnight in the cold room at 4 degrees centigrade to allow for auto-digestion.

After digestion for 12 hours, the suspension is centrifuged for 75 minutes at 80,000 g to give supernatant 2 which contains 20–30% of the total AChE activity. The resulting pellets are again suspended in 250 ml cold 0.32M sucrose in 1 mM EDTA, pH 6.9, using five strokes of the Kontes dounce tissue grinder with pestle #A. The homogenate is then centrifuged at 80,000 g for 75 minutes to give supernatant 3 and a residue pellet.

C. Dialysis

Supernatants 2 and 3 are dialyzed separately overnight against 1 mM $Na_2HPO_4$, pH 7.0, (11 liters) in the cold. The supernatants are then centrifuged at 80,000 g for 75 minutes to remove any residue and assayed for activity and protein. The above procedure is performed 3 times to give 3 sets of supernatants 2 and 3 form 36 brains. All 6 supernatants are combined at room temperature and precipitated with ammonium sulfate (Mallinckrodt analytical reagent) 14% 9 w/v) for 35 minutes. The ammonium sulfate is added slowly to the combined supernatant which is being gently stirred. After precipitation, the same is centrifuged at 14,000 g in the VRA head of the Lourdes centrifuge. The supernatant is again precipitated for 35 minutes with ammonium sulfate to bring the final concentration to 40% (w/v). The suspension is centrifuged at 14,000 g for 40 minutes and the protein precipitate is redissolved in 250 ml of 30 mM $Na_2HPO_4$, pH 7.0,(4 liters) to remove any ammonium sulfate. The dialysate is centrifuged at 14,000 g to remove any residue and assayed for activity and protein concentration.

D. Column Chromatography

1. DEAE Cellulose Column

Five grams coarse mesh plus 5 grams fine mesh (Sigma) DEAE Cellulose are added slowly to 1 liter deionized water while stirring slowly to properly expand the DEAE Cellulose. The mixture is stirred 2 hours; allowed to settle 15 minutes and the supernatant poured off. The DEAE Cellulose is resuspended in 1 liter of deionized water, stirred 5 minutes, and allowed to settle for two hours. The supernatant is discarded.

The above residue is poured into a 10 cm Buchner funnel having a seated #42 filter paper (9 cm diameter). One wash of 500 ml of 0.5N HCl is followed by 1 liter deionized water. The next wash is with 500 ml of 0.5N NaOH followed by 1 liter deionized water, and finally 200 ml 0.5N HCl followed by 1 liter 30 mM $Na_2HPO_4$, pH 7.0.

The column is then filled with the washed cellulose. The column is Kontes #20 with a glass synder bed stop. The bed is 2.1 cm by 30 cm. Flow rate is 39 ml per hour. After the protein concentration and volume are determined, the sample is loaded on the DEAE cellulose column prewashed with about 300 ml 30 mM $Na_2HPO_4$, pH 7.0.

The column is then filled with the washed cellulose. The column is Kontes #20 with a glass synder bed stop. The bed is 2.1 cm by 30 cm. Flow rate is 39 ml per hour. After the protein concentration and volume are determined, the sample is loaded on the DEAE cellulose column prewashed with about 300 ml 30 mM $Na_2HPO_4$, pH 7.0 (2×loading volume). The gradient is now attached such that 6 cm of buffer is above the cellulose surface; this prevents disturbance of the gel as the gradient solution enters the column. Linear gradient elution of the column is carried out using two Kontes Gradient Elution vessels of 250 ml capacity. One hundred fifty ml of 0.03M NaCl in 30 mM $Na_2HPO_4$, pH 7.0, is placed in the mixing chamber while 150 ml of 0.6M NaCl in 30 mM $NA_2HPO_4$, pH 7.0, is placed in the reservoir chamber. A 3 cm teflon stirring bar and a Micro V magnetic stirrer operated at setting 4 are used to create the gradient for elution. The gradient apparatus is 25 cm above column outflow. The fractions (3 mls each) with activity appear prior to the half-way point in the collection of fractions.

The samples containing enzyme activity (specific activity of 600–1500 μM/mg/hr) are pooled and dialyzed against 30 mM $Na_2HPO_4$ for 12 hours. Then the samples are lyophilized in a Vitis lyophilizer for 8 hours. The lyophilizer sample is carefully removed from the Vitis vessel and dissolved in 2.0 ml of deionized $H_2O$ at room temperature.

2. Preparation of G-200

G-200 SEPHADEX (Pharmacia-Uppsala, Sweden) is hydrated for 3 days in 1.5 liters deionized water, stirring gently, to give 1.25 liters expanded particles. A Kontes (Chromaflex) column 2.2 cm (ID) is packed to give a bed height of 90 cm under a 15 cm head of pressure. Flow is obtained using a syphon from the reservoir of 30 mM $Na_2HPO_4$ to the water column above the bed. The outlet is 15 cm below the highest eluant levels at all times. The void volume determined with blue dextran, is 155 ml and the column takes 10 hours to elute. AChE sample volumes, protein content and activity are determined after column elution. The reservoir is a one liter volumetric refilled with a glass funnel as needed. All fractions are collected using a Gilson fraction collector. (The scheme for neuroreceptor preparation is shown in FIG. 1).

A. Lyophilization Studies

An AChE preparation (Prep D) was obtained from the purification scheme of S. L. Chan (Chan, S. L. et al. (II) "Purification of Beef Brain Acetylcholinesterase" *Proceedings of the Western Pharmacology Society*, 13:43–47, 1970) and lyophilized in a Virtis Model lyophilizer. The same was placed in a beaker with a performated filter paper cover. Cicular dichoism runs were made prior to lyophilization. After lyophilizations, each sample was suspended in deionized water. AChE activity and protein concentration were also determined for each CD run.

B. Salt Study

An AChE preparation (Prep E) was made using the scheme of S. L. Chan, supra "Purification of Beef Brain Acetylcholinesterase" *Proceedings of the Western Pharmacology Society*, 13:43–47, 1970. The AChE in 0.4M NaCl/30 nM $Na_2HPO_4$ was lyophilized and resuspended in 2.5 ml deionized water. The CD spectrum was made, and activity was checked qualitatively. The sample was dialyzed against 100 mM $MgSO_4$ for 12 hours. AChE activity was qualitatively checked with CD. The sample was then redialyzed against 0.4M NaCl/30 mM $Na_2HPO_4$ for 12 hours, checked for AChE activity and for CD absorption.

EXAMPLE 2

Bioassay of Mammalian Neuroreceptor

A. Equipment

Strain free, quartz ORD cells of 0.5 mm, 1.0 mm, 5.0 mm, and 10.0 mm will be needed (purchased from Pyrocell, New Jersey, U.S.A.). One strain free, quartz ORD cell of 2.005 mm is also needed (purchased from Aminco). All cells are stored or filled with glass double-distilled water. Washing is accomplished with 2 flakes of Alconox glass cleaner IMMEDIATELY after removal of protein sample from the cell. This is followed with 25 washes of double-distilled water prior to storage or filling with another sample. (A solution of two drops of concentrated HCl in 15 ml EtOH is ineffective as a cleaning agent.) If the AChE sample is allowed to denature in the cell, a 50% dichromate cleaning solution in the cell for 10 minutes is useful, however, the acid is a very caustic agent for precision optical glassware, and its use should be minimized.

B. Baselines

Baselines of all cells are obtained in a Jouan Dichrograph II using first a run with air followed by a run with glass double-distilled water. Prior to each run, a baseline with glass double-distilled water is run to make certain the cell is clean.

A baseline of the solution is obtained using 222 nm without removing the cell after a run is begun to allow for thermal stabilization. Prior to adding the drug to the enzyme, a blank run consisting only of the drug at the same concentration used in the enzyme study is made. To obtain control data, temperature changes of 5 degrees centigrade in the neuroreceptor solution alone are made using a Forma water bath. Then the drug is added to a sample of the purified neuroreceptor solution, and the stabilizing effect of the drug on the temperature-related conformational changes is noted. All temperature runs are allowed to equilibrate for one hour before data is collected. Macromolecular samples for control and drug interaction have the same alpha helix content prior to drug addition. Lidocaine is then used to stabilize the alpha helix from 30°–35° C.; from 35°–40° C. the alpha helix uncoils to equal the helix in the control sample.

As the result shown in FIG. 2, this combination of drug/enzyme/neuroreceptor with circular dichroism becomes the bioassay for the neuroreceptor when the drug, lidocaine, successfully stabilizes the coiled alpha helix in the face of increased temperature in its coiled form as compared to the control sample of enzyme/neuroreceptor alone over the same temperature range. The specificity of this transition of the alpha helix as well as its lack of any apparent relationship to AChE activity indicates a functional molecular event. Lidocaine, by stabilizing the alpha helix in the coiled form, becomes the identifier of the neuroreceptor macromolecule. Bioassay, then, would be the testing of a new pharmaceutical against the purified mammalian neuroreceptor using circular dichroism to observe the results and the above described lidocaine test as the control.

C. Optical Studies of AChE with Neuroreceptor

All studies are made in 1 mm, 5 mm and 2 mm cells using a Jouan Dichrograph II at $1 \times 10^{-5}$ O.D./mm sensitivity. The sample solution consists of 30 mM $Na_2HPO_4$, pH 7.0, and the enzyme. Protein concentration is determined empirically and then measured by the Lowry method after the run. Lowry, et al., *J Biol Chem*, 193: 265–275 (1951). Samples are taken directly from G-200 fractions or DEAE-Cellulose fractions previously dialyzed against 30 mM $Na_2HPO_4$, pH 7.0.

D. Thermal Studies

Thermal studies are carried out in the 10 mm cell. Care must be taken not to misplace the cell in the cell holder to avoid spectral changes. Additionally, since the absorption is affected by pressure, the ORD cell's glass stopper must be gently seated. for the thermal runs of Prep A, a microthermometer is used to record the temperature in the ORD cell after each spectral recording.

The routine consists of beginning a CD spectral scan followed by running each activity blank at that temperature using 3 minute reading intervals. The next CD spectral scan is made after recording the temperature in the ORD cell. The data recorded consists of duplicates of CD spectra with cell temperatures varying 5 degrees centigrade at 222 nm.

Temperature variation was obtained using a Forma Scientific heating bath with circulator. A common water flow was divided between the Jouan cell holder block and the specially constructed thermal cell for the Hitachi spectrophotometer (See appendix A and B). Maximum water flow was used throughout the whole system.

Assay of each sample's AChE activity was accomplished using the thermal cell for the Hitachi. The enzyme sample (0.025 ml) was drawn from a stock enzyme solution, which had been divided into ORD cell (3 ml) and assay (1 ml) samples. The enzyme assay samples and blanks containing no enzyme were incubated in a Haake temperature bath adjusted lot below temperature levels used in the run.

The routine consisted of beginning a CO spectral scan followed by running each activity blank at that temperature using 3 minute reading intervals. The next CD spectral scan was made after recording the temperature in the ORD cell. During the scan, the activity of the enzyme samples was determined. Prior to each assay of blank or activity and before addition of substrate, the sample was equilibrated with the temperature of the Hitachi thermal cell and the temperature was recorded. The data recorded consisted of duplicates of CD spectra with cell temperatures, enzyme activity with cuvette temperatures, and blanks with cuvette temperatures. Initial studies of the spectrum were from 300 nm to 205 nm. Later 270 nm to 205 pm were used because a baseline level was obtained at 270 nm and no absorption occurred above 270 nm.

EXAMPLE 3

Circular Dichroism Bioassay of Neuroreceptor Preparation in the Presence of Lidocaine Pilocarpine, reagent grade, was used at $1.33 \times 10^{-6}$M in the sample solutions. Lidocaine hydrochloride monohydrate (Astra Pharmaceutical Products, Mass., U.S.A.) was used at the same concentration.

A buffer solution of 20 mM $Na_2HPO_4$, pH 7.0, gives minimal absorption problems in the range 300 nm to 195 nm. Enzyme solutions contain from 21 µg/ml to 31 µ/ml of protein in buffer. Total ORD cell volume is 3.0 ml. Lidocaine is added to ORD cells in 0.002 ml volumes in order to minimize dilution effects. a Rousel-Jouan Dichrograph II sensitive to $1 \times 10^{-5}$ dichroic absorption unit per recording mm is used with a 10 mm, strain free, quartz ORD cell (Pyrocell, New Jersey, U.S.A.).

A buffer solution of 30 $Na_2HPO_4$, pH 7.0,gave minimal absorption problems in the range 300 nm to 195 nm. Enzyme solutions contained from 21 µg/ml to 31 µg/ml of protein in buffer. Total ORD cell volume was 3.0 ml. Drugs were added to ORD cells in 0.002 ml volumes in order to minimize dilution effects. A Roussel-Jouan Dichrograph 11 sensitive to $1 \times 10^{-5}$ dichroic absorption unit per recording mm was used with a 10 mm, strain free, quartz ORD cell (Pyrocell, New Jersey, U.S.A.).

Again CD spectra were obtained using the above thermal apparatus over the range of 230 nm to 215 nm. A baseline of the enzyme solution was obtained using 300 nm to 285 nm without removing the cell after a run was begun. Prior to adding the drug to the enzyme, a blank run consisting only of the drug at the same concentration used in the enzyme study was made. To obtain control data, temperature changes in the enzyme solution alone were made using a Forma water bath. Then the drug was added to another enzyme solution with the same protein concentration which came from the stock solution, and temperature effects were noted. All temperature runs were allowed to equilibrate for one hour before data were collected.

A. Computations

Data for CD was expressed so that experimental values could be compared with published helix composition values. All graphs and raw data were expressed as molar el lipticity |Θ| based on mean residue molecular weight because the true molecular weight of AChE has not been established for the brain enzyme.

Helix calculation (15):

Given: PGA (polyglutamic acid) served as 100% helix standard with a

|Θ| of −44,000 (16).

$M_o$=molecular weight of mean amino acid residue=115.

A=Optical density=(Jouan sensitivity/ nm)(mm).

C =gm/liter.

L cell length in cm.

$\Delta\epsilon = \epsilon_{left} - \epsilon_{right} = A/(C/M_o)L$ $|\Theta|_{\%\ helix} = |\Theta|/-44,000 \times 100\%$

A. Assays (i) Acetylcholinesterase

Activity of AChE was determined at 25° C.–30° C. and pH 8.0 by the spectrophotometric method of Ellman et al (*Biochemical Pharmacology*, 7:88–95 (1961). Measurements were made in the Hitachi Perkin-Elmer Model 139 spectrophotometer at 412 nm and 0.1 nm slit. One unit of AChE activity was defined as 1 µM of ATC (acetyl thiocholine iodide,Sigma) hydrolyzed per hour at 25° C. Specific activity is expressed as µmoles ATC hydrolyzed/ mg protein/ hour.

Calculation of activity:

$$AChe\ rate = \frac{\Delta A}{1.36 \times 10^4} \times \frac{1}{v/V \times C_o} \times \frac{10 P6\ gr \times 60\ min}{10^3\ gm/mg}$$

$$= \frac{\Delta A}{1.36} \times \frac{6}{v/V \times C_o}\ \mu M/mg/hr$$

(ii) Protein

Protein was routinely determined by the method of Lowry et al. using bovine serum albumin (Bovine albumin, Fraction V, Sigma).

(iii) Total Nitrogen

Total nitrogen was determined by the method of C. A. Lang (*Analytical Chemistry*, 30:1692–1695 (1958)) using a microdetermination. The direct procedure was used. Nessler reagent was prepared by taking 5% (w/v) $HgCl_2$ and adding 5% K1 to make a to make a brown precipitate. K1 was added until the precipitate just disappeared. The solution was stored protected from light. The heating bath consisted of sand in a metal tray heated by two bunsen burners. A ½ inch asbestos block with ten holes served to hold the sample 15×125 mm glass bacteriological test tubes. The standard was Ammonium sulfate (Mallinckrodt analytical grade).

C. Thermal Study of AChE

Enzyme activity and helix content were studied concurrently as the temperature was changed from 15° C. to 60° C. The AChE sample was obtained from fractions 21 and 22 of the G-200 column of Prep A. The temperatures for each |Θ| value were determined experimentally in the sample solution. Total activity (Δ0.D./min/25λ) for the enzyme was corrected for the rate change of the Ellman assay at that temperature. Scans were made from 300 nm to 205 nm for the first study. Subsequent studies were from 270 nm to 205 nm. The molar ellipticity at 222 nm was used to represent helix content without a correction for random coil at that wavelength. Random coil content at 222 nm could not be established with this preparation. The molar ellipticity at 207 nm was taken as a combined measure of coil and helix; the wavelength was arbitrarily established from the information obtained in the lyophilization study.

Table 6 presents the standard error of the optical results at 222 nm and 207 nm as calculated using a Hewlett Packard computer program. The total activity was adjusted by a factor of 1.13 because of the differences in dilutions between the two samples.

Another thermal study was run on Prep B sample having a specific activity of approximately 11,000 µM/mg/hr. The data for this work were collected from one sample simply because no more material existed. The preparation's enzyme activity was not as stable over as broad a temperature range compared to previous thermal studies. Possibly there were fewer protein molecules per unit volume with fewer inter molecular interactions to give a more unstable enzyme.

In another experiment of the molar ellipticity for coil 207 nm |Θ| which is composed of helix and coil. The coil has a negative molar ellipticity at 207 nm. A curve for helix at 222 nm was superimposed on the curve at 207 nm. The difference between the two curves was plotted. Since 207 nm is not at the minimum for coil, the coil content determined at this wavelength is not the maximum coil content possible for the sample studied. A similar analysis for thermal run #3 was done. It appears that between 30° C. and 60° C., random coil content increases directly with temperature.

D. Test of Reversibility of Alpha Helix

Transition Between 30° C. and 40° C.

A fresh fraction #34 of Prep B's first G-200 elution was equilibrated at 30° C. The temperature was increased to 35°

C. and then cooled to 30° C. Table 7 shows the CD data at 222 nm. The data for two preparations show that changes due to temperature increases were irreversible in the system used.

E. Drug, AChE and CD monitor of alpha helix

Alpha helix at 222 nm was used to monitor the effect of pilocarpine and lidocaine in the presence of AChE while the temperature was changed between 30° C. and 35° C. at pH 7.0. Pilocarpine alone had a positive ellipticity between 215 nm and 230 nm. Lidocaine HCl had no ellipticity in this wavelength race. Enzyme concentrations were determined empirically, but the AChE control and AChE study sample had the same alpha helix content prior to the addition of any drugs. Table 8 presents the experimental results under the various conditions; Table 9 shows percentage changes. Pilocarpine and lidocaine appear to stabilize the helix during the transition between 30° C. and 35° C. in fresh preparations.

The data from several of the experiments described above are shown in the tables that follow.

TABLE 3

% HELIX AND AChE SPECIFIC ACTIVITY OF PREPARATIONS A, B, C, AND D.

| Preparation | Specific Activity | $[\theta]_{222}$ | % Helix |
|---|---|---|---|
| Prep A 45° C. | 5,600 | −5,750 | 13.1 |
| Prep A 25° C. | 6,300 | −11,520 | 26.2 |
| Prep B #34 | 11,000 | −6,300 | 14.3 |
| Prep B (Drug) | 600 | −12,900 | 29.3 |
| Prep C | 1,470 | −6,950 | 15.8 |
| Prep D | 350 | −6,780 | 15.6 |

TABLE 1

RECOVERY OF AChE FOR PREP A

| Fraction | Vol (ml) | Protein mg | Protein % | AChE Activity Specific | AChE Activity Total | AChE Activity % |
|---|---|---|---|---|---|---|
| Start | 139.1 gm | — | — | — | — | — |
| Homogenate | 750 | 18,000 | 100 | 23.5 | 422,000 | 100 |
| post 600 g sup | 990 | 15,750 | 87.3 | 26.2 | 413,000 | 97.8 |
| Sup 1 | 830 | 2,015 | 11.3 | 18.0 | 36,100 | 8.5 |
| Sup 2 | 702 | 441 | 2.5 | 215.0 | 94,600 | 22.3 |
| Sup 3 | 500 | 106 | 0.5 | 185.0 | 19,400 | 4.6 |
| Residue | Not measured | | | | | |
| COLUMNS: | | | | | | |
| Sup$_{2,3}$ | 1202 | 547 | 100 | 209 | 114,000 | 100 |
| (NH$_4$)$_2$SO$_4$ ppt | 220 | 220 | 40 | 224 | 49,200 | 43.0 |
| DEAE-Cellulose | 56.1 | 12.24 | 2.2 | 961 | 11,600 | 10.2 |
| G-200 | 13.2 | 0.645 | 0.12 | 5,200 | 3,350 | 2.9 |

TABLE 2

RECOVERY OF AChE ACTIVITY FOR PREP B

| Fraction | Vol (ml) | Protein mg | Protein % | AChE Activity Specific | AChE Activity Total | AChE Activity % |
|---|---|---|---|---|---|---|
| Start | 1442 gm | — | — | — | — | — |
| Homogenate | 700 | 16,450 | 100 | 26.2 | 428,000 | 100 |
| post 600 g | 1000 | 13,200 | 80 | 27.8 | 367,000 | 86.0 |
| Sup 1 | 890 | 1,800 | 11 | 23.5 | 42,100 | 9.8 |
| Sup 2 | 623 | 510 | 3.1 | 135 | 69,100 | 16.2 |
| Sup 3 | 625 | 145 | 0.9 | 185 | 26,900 | 6.3 |
| Residue | 300 | 4,500 | 27.2 | 30 | 135,000 | 31.2 |
| COLUMNS: | | | | | | |
| Sup$_{2,3}$ | 1,250 | 655 | 100 | 147 | 96,000 | 100 |
| (NH$_4$)$_2$SO$_4$ ppt | 350 | 342 | 52.2 | 206 | 70,000 | 73.0 |
| DEAE-Cellulose | 90 | 64.5 | 9.8 | 751 | 48,500 | 50.5 |
| G-200 | 21 | 5.05 | 0.77 | 956 | 4,830 | 5.5 |
| G-200 | 6 | 0.10 | 0.15 | 5,000 | 500 | 0.5 |

TABLE 4

EFFECTS OF LYOPHILIZATION ON AChE OF PREP D

| Lyophilization | AChE ΔA/0.1 ml | S.A. | % Loss S.A. | Protein μg/ml | % Loss | Helix (nm) 220 nm | % Loss |
|---|---|---|---|---|---|---|---|
| 1st | 0.272 | 320 | — | 112 | — | 20 | — |
| 2nd | 0.150 | 268 | 16 | 75 | 33 | 13 | 35 |
| 3rd | 0.000 | 0 | 100 | 64 | 14 | 9.5 | 27 |

TABLE 5

EFFECT OF $MgSO_4$ ON AChE OF PREP E.

| Step | AChE Qualitative Activity | Helix 220 nm |
|---|---|---|
| Resuspended After Lyophilized | ++ | 61 mm |
| Dialyzed Against $MgSO_4$ | 0 | 16 mm |
| Dialyzed Against 0.4M NaCl/30 mM $Na_2HPO_4$ | + | 15 mm |

TABLE 6

$|\theta|_{222}$ AND $|\theta|_{207}$ STANDARD ERROR FOR THERMAL RUNS #1 AND #2

| Temperature | Mean $|\theta|_{222}$ | Standard Error | % Standard Error |
|---|---|---|---|
| 15 | 9990 | 533 | 5.33 |
| 20 | 9412 | 118 | 1.25 |
| 25 | 9260 | 176 | 1.91 |
| 30 | 8700 | 293 | 3.47 |
| 35 | 7468 | 196 | 2.63 |
| 40 | 6055 | 104 | 1.72 |
| 45 | 5380 | 198 | 3.67 |
| 50 | 5142 | 260 | 5.05 |
| 55 | 4425 | 71 | 1.61 |
| 60 | 4230 | 104 | 2.46 |

| Temperature | Mean $|\theta|_{207}$ | Standard Error | % Standard Error |
|---|---|---|---|
| 15 | 7885 | 424 | 5.36 |
| 20 | 7065 | 198 | 2.81 |
| 25 | 7592 | 268 | 3.54 |
| 30 | 6852 | 518 | 7.55 |
| 35 | 5770 | 490 | 8.50 |
| 40 | 4978 | 250 | 5.05 |
| 45 | 4570 | 552 | 12.00 |
| 50 | 5028 | 479 | 9.74 |
| 55 | 4845 | 463 | 9.53 |
| 60 | 5085 | 505 | 10.01 |

STANDARD ERROR FOR AChE ACTIVITY FOR THERMAL RUNS #1 AND #2

| Temperature | Mean Δa | Standard Error | % Standard Error |
|---|---|---|---|
| 15 | 0.164 | 0.0027 | 1.65 |
| 20 | 0.192 | 0.0039 | 2.04 |
| 25 | 0.221 | 0.0030 | 1.36 |
| 30 | 0.239 | 0.0017 | 0.71 |
| 35 | 0.250 | 0.0090 | 3.60 |
| 40 | 0.277 | 0.0068 | 2.46 |
| 45 | 0.265 | 0.0000 | 0.00 |
| 50 | 0.229 | 0.0129 | 5.64 |

TABLE 7

IRREVERSIBILITY OF HELIX TRANSITION

| Temperature | $|\theta|_{222}$ | $\Delta|\theta|_{222}$ | % Loss Helix |
|---|---|---|---|
| Prep A | | | |
| 25° C. | −4560 | — | — |
| 60° C. | −2150 | 2410 | 53.5 |
| 25° C. (1 week later) | −1640 | 510 | 23.7 |
| Prep B | | | |
| 30° C. | −6650 | — | — |
| 35° C. | −5170 | 1480 | 22.2 |
| 30° C. (2 hours later) | −4860 | 310 | 5.8 |

TABLE 8

AChE IN PRESENCE OF DRUGS

| Enzyme Conditions | 30° C. | 35° C. | 38° C. | $|\Theta|_{30} - |\Theta|_{35}$ | $|\Theta|_{38} - |\Theta|_{35}$ |
|---|---|---|---|---|---|
| Fresh AChE (Prep B) | −13,300 | −10,400 | — | 2,900 | — |
| Pilocarpine | +5,450 | — | — | — | — |
| Above AChE and Pilocarpine | −11,300 | −10,500 | — | 800 | — |
| AChE Prep B (7 Days Later) | −4,640 | −3,770 | — | 870 | — |
| Above AChE and Pilicarpine | −3,590 | −2,280 | — | 720 | — |
| Lidocaine | 0 | 0 | — | — | — |
| Above AChE and Lidocaine | −3,590 | 0 | — | 600 | — |
| Difference of Lidocaine from Above AChE | +540 | +480 | — | — | — |
| Fresh AChE (Prep C) | −6,850 | −6,020 | −5,700 | 830 | 320 |
| Above AChE and Pilocarpine | −4,490 | −4,320 | −3,540 | 170 | 780 |
| Above AChE and Lidocaine | −5,560 | −5,500 | −4,830 | 100 | 770 |
| Nicotine | −21,400 | — | — | — | — |
| Atropine Sulfate | — | — | — | — | — |

TABLE 9

PERCENT STABILIZATION OF HELICAL CONFORMATION OF AChE IN THE PRESENCE OF LIDOCAINE AND PILOCARPINE

| Enzyme Conditions | % Loss of Helix (30° C. to 35° C.) | % Loss of Helix (35° C. to 40° C.) |
|---|---|---|
| Fresh AChE Control | 21.8 | 4.7 |
| Fresh AChE with Pilicarpine | 7.1 | 17.5 |
| Fresh AChE Control | 12.1 | 4.6 |
| Fresh AChE with Lidocaine | 1.8 | 13.6 |
| 7 Day old AChE Control | 18.8 | — |
| 7 Day old AChE with Pilicarpine | 20.7 | — |
| 7 Day old AChE with Lidocaine | 16.8 | — |

TABLE 10

PERCENT STABILIZATION OF HELICAL CONFORMATION OF AChE IN THE PRESENCE OF LIDOCAINE AND PILOCARPINE

| Enzyme Conditions | % Loss of Helix (30° C. to 35° C.) | % Loss of Helix (35° C. to 40° C.) |
|---|---|---|
| Fresh AChE Control | 21.8 | 4.7 |
| Fresh AChE with Pilocarpine | 7.1 | 17.5 |
| Fresh AChE Control | 12.1 | 4.6 |
| Fresh AChE with Lidocaine | 1.8 | 13.6 |
| 7 Day Old AChE Control | 18.8 | — |
| 7 Day old AChE with Pilocarpine | 20.7 | — |
| 7 Day old AChE with Lidocaine | 16.8 | — |

RESULTS AND DISCUSSION OF DATA

I. Purification:

A. Purification of AChE for Prep A.

Table 1 shows the yield and specific activity of AChE for Prep A using the purification procedure of S. L. Chan et al. (as shown in Example 1). The nuclear pellet and supernatant 1 were discarded. Supernatants 2 and 3 were used for further purification because they had high AChE yield and high AChE specific activity. FIG. 1 shows the DEAE column purification of AChE. The abrupt increases in AChE specific activity in the elution pattern might be a result of smaller fraction volumes collected as compared to those in the preparation of S. L. Chan et al., supra. However, the activity peaks can be distinguished from the trailing protein peak. Fractions 33–49 were prepared for G-200. Samples obtained from this column were used for CD thermal studies. The column elution patterns only show the peaks because, for the purpose of CD, it was not necessary to assay the complete elution pattern. Fraction numbers are arbitrary because collection began after the void volume had been collected.

B. Purification of Prep B

Table 2 shows the recovery of AChE activity at the various steps. Unlike prep A, there was twice as much protein for the DEAE column. Thus a gradient of 260 ml was inadequate to separate distinctly the trailing protein peak from AChE activity peaks. It is suggested that a gradient of 360 ml be used. Fractions 31–61 were pooled for G-200.

From an elution patter for Prep B, two peaks (1 and 11) of AChE were obtained. Peak 11 (#28–33) was reapplied to the G-200 column. Fractions 19 and 20 from peak 1 and fraction 34 from peak 11 were used in drug-enzyme-CD studies.

Re-chromatographing of peak 11 gave one fraction with AChE specific activity of 11,000, another with 4,000 and two with 2,000. A plot was not made because the elution pattern was assayed incompletely, and the protein determination was very low: The specific activity may, therefore, vary by ±2,000 units.

C. Prep C

This preparation consisted of an accumulation of all AChE in the laboratory left over from previous preparations. All material had been stored lyophilized or in the cold room. This effort was aimed at gaining material for drug studies; and, therefore, no data for a table of recovery was accumulated.

An elution pattern of the DEAE column using a 360 ml gradient was made. Fractions 55–70 were pooled for G-200. Another elution patter shows the G-200 for the pooled fractions. Although other peaks of activity occurred in the elution, the two peaks graphed appeared similar to previous purifications. Peak 11 samples were used for drug-enzyme-CD studies.

D. Prep D and E

No purification elution patterns of preps D and E were made. This lack of rigor in the preparation of the enzyme resulted in low specific activity. The specific activity of Prep D is presented in Table 3 with the appropriate lyophilization steps. The specific activity for Prep E was 117 μM/mg/hr after lyophilization. Table 4 presents the qualitative results of $MgSo_4$ on the AChE from Prep E.

II. Total Nitrogen Determination:

AChE sample #20 of Prep A's G-200 had a Lowry determination of 51 µg/ml. Total nitrogen determination on 0.1 ml of the sample gave 45 µg/ml protein. Total protein was determined assuming that 15% of the total protein weight was nitrogen.

III. Optical:

A. Baselines

The ORD cell baselines in air and water were relatively straight without any absorption peaks at the sensitivities used. The baselines for 0.4M NaCl 30 mM $Na_2HPO_4$, and 100 mM $MgSo_4$ were also without absorption peaks from 300 nm to 205 nm. Below 205 nm the optical density of the protein solutions containing phosphate became so great that no light passed through a 10 mm cell. Cells with smaller path lengths permitted scans to 195 nm using nitrogen purge.

B. AChE Spectrum

A complete spectrum of AChE at room temperature (22° C.) and pH 7.0, from 300 nm to 195 nm for Prep A, using 0.5 mm, 1.0 mm and 10.0 mm ORO cells was graphed. The molar ellipticity value for each nm was corrected for the baseline and a cell path length of —0 mm —to give a composite curve. The ratio of the molar ellipticity at 220 nm to that at 190 nm is 3:1 for a helix (6). The experimentally obtained value for $|\Theta|_{220}$ to $|\Theta|198$ is 1.6:1.

The value at 198 was lower than that expected for 100% helix. A calculation of random coil at 198 nm would give 47% random coil.

Expect $|\Theta|198$ for 100% helix=35,000
Observed $|\Theta|198$ for AChE=18,500
ΔCoil=16,500 or
coil %=100% (16,500/35,000)=47%

The helix content at 222 nm, where random coil absorbs at a minimum, is 26.3% (16). See "Method" for calculation of helix. The spectrum of AChE under the above conditions, then, includes a random coil structure (47%) with the presence of helix (26%).

C. Helix Content

The helix content for AChE for the different preparations is presented in Table 3. The calculation is based on the work of Holzworth and Doty (insert); 100% helix is for polyglutamic acid (PGA) and includes the amount of random coil present at 222 nm. Interestingly, the amount of helix does not appear to be directly related to AChE specific activity.

D. Result of Lyophilization on AChE

Prep D was lyophilized repeatedly to see if the procedure had any effect on AChE. Changes in the hydration state of the helix or in salt content or in both might be expected to have effects on the enzyme protein. A salt effect appears doubtful since $(NH_4)_2SO_4$ was used in the purification procedure without apparent detrimental effects on the enzyme. In addition, any salt effect might be observed after a single lyophilization. The data in Table 4 indicate that the enzyme is more resistant to the lyophilization procedures than would be expected for salting out effects. The results indicate a pattern similar to a dehydration effect on the protein.

E. Effect of $MgSO_4$ on AChE's helix $MgSO_4$, which has no optical properties from 300 nm to 195 nm, was selected as alternate ions to maintain AChE in solution. FIG. 9 shows AChE in the presence of 0.4M $NaCl/30 Na_2HPO_4$, 100 mM $MgSO_4$ and then 0.4M $NaCl/30$ mM $Na_2HPO_4$. Table 5 presents a summary of AChE activity for this experiment. The random coil at 195 nm in 100 mM $MgSO_4$ is 35%. The ratio°of helix at 195 nm to helix at 222 nm is 1.97:1, while from FIG. 7 the ratio is 1.6:1.

F. Thermal Study of AChE

Enzyme activity and helix content were studied concurrently as the temperature was changed from 15° C. to 60° C. The AChE sample was obtained from fractions 21 and 22 of the G-200 column of Prep A. The temperatures for each $|\Theta|$ value were determined experimentally in the sample solution. Total activity (ΔO.D./min/25λ) for the enzyme was corrected for the rate change of the Ellman assay at that temperature. Scans were made from 300 nm to 205 nm for the first study. Subsequent studies were from 270 nm to 205 nm. The molar ellipticity at 222 nm was used to represent helix content without a correction for random coil at that wavelength. Random coil content at 222 nm could not be established with this preparation. The molar ellipticity at 207 nm was taken as a combined measure of coil and helix; the wavelength was arbitrarily established from the information obtained in the lyophilization study.

Table 6 presents the standard error of the optical results at 222 nm and 207 nm as calculated using a Hewlett Packard computer program. The total activity was adjusted by a factor of 1.13 because of the differences in dilutions between the two samples.

Another thermal study was run on Prep B sample having a specific activity of approximately 11,000 µM/mg/hr. The data for this work were collected from one sample simply because no more material existed. The preparations enzyme activity was not as stable over as broad a temperature range compared to previous thermal studies. Possibly there were fewer protein molecules per unit volume with fewer inter molecular interactions to give a more unstable enzyme.

A curve was drawn of the molar ellipticity for coil using 207 nm $[\Theta]$ which is composed of helix and coil. The coil had a negative molar ellipticity at 207 nm. The curve for helix at 222 nm was superimposed on the curve at 207 nm. The difference between the two curves was plotted 16 as coil content. Since 207 nm is not at the minimum for coil, the coil content determined at this wavelength is not the maximum coil -content possible for the sample studied. A similar analysis for thermal run #3 was done. It appears that between 30° C. and 60° C., random coil content increases directly with temperature.

G. Test of Reversibility of Alpha Helix Transition Between 30° C. and 40° C.

A fresh fraction #34 of Prep 8's first G-200 elution was equilibrated at 30° C. The temperature was increased to 35° C. and then cooled to 30° C. Table 7 shows the CD data at 222 nm. The data for two preparations show that changes due to temperature increases were irreversible in the system used.

H. Drug, AChE and CD monitor of alpha helix

Alpha helix at 222 nm was used to monitor the effect of pilocarpine and lidocaine in the presence of AChE while the temperature was changed between 30° C. and 35° C. at pH 7.0. Pilocarpine alone had a positive ellipticity between 215 nm and 230 nm. Lidocaine HCl had no ellipticity in this wavelength range. Enzyme concentrations were determined empirically, but the AChE control and AChE study sample had the same alpha helix content prior to the addition of any drugs. Table 8 presents the experimental results under the various conditions; Table 9 shows percentage changes. Pilocarpine and lidocaine appear to stabilize the helix during the transition between 30° C. and 35° C. in fresh preparations.

EXAMPLE 4

Diagnosis of Patients Ion Channel Thermal Protein

In this example, the method of the present invention is used for the diagnosis of the ion channel of a thermal protein of a patient. First a reference standard thermal protein is prepared as described in Example 1. Circular dichroism analysis at 225 mM wavelength measuring the molar ellipticity is taken at 30° C., 35° C. and 40° C. with and without added lidocaine. A patient biopsy of fresh protein acetylcholine esterase was purified per Example 1, and one sample is mixed with lidocaine and the other, as a patient control is not, per the methods shown in the previous examples. The two samples are subject to circular dichroism at 225 mM at 30° C., 35° C. and 40° C. and the data is plotted and compared with the data for the control sample. By comparison with the control data and curves, one is able to ascertain dysfunction or disease of the ion channel of the patient's thermal protein, a diseased or dysfunctional ion channel will have a different curve due to its inability to metablize and/or release the lidocaine.

EXAMPLE 5

Screening of Compounds for Use in Ion Channel Dysfunction

Several samples of thermal proteins acetylcholine esterase purified as per Example 1 are prepared. One sample protein is mixed with lidocaine as a control and CD measurements are taken at 225 mM at 30° C., 35° C. and 40° C. The data obtained is plotted per FIG. 2 to the remaining samples these are added several test compounds, including tetrodotoxin, batrachotoxin, veratridine, and β-scorpin toxins, DDT, synthetic pyrethroids and others. CD data for these compounds are plotted with that of lidocaine to ascertain their effectiveness of stabilizing the ion channel. The method is useful in predicting and screening the use of such compounds as ion channel stabilizing compounds.

Another aspect of this invention involves the association of sodium ion channel dysfunction with cancer. The following is a summary of this relationship:

1. Certain cancers are clinically diagnosed initially solely on their neurological symptoms before an actual tumor can be located.
2. Some tumors make neuropeptides and elicit clinical neurological symptoms and problems in management.
3. The sodium channel dysfunction is believed to turn on the oncogene in the laboratory (personal communication from Scripts Institute).
4. It has been suggested that the ion channels control T-lymphocytes.
5. Goetzl's research (Neuropeptides, mast cells and allergy: novel mechanisms and therapeutic possibilities; *Clinical and Experimental Allergy* 20 supplement 4:3-7, 1990) would require for its basic membrane modulator an ion channel that allows intraneuronal DNA events to be communicated extracellularly.
6. Some tumor treating agents specifically act on the sodium channel (*Trends in Neuroscience* 14:146-151 (1991)).
7. Earlier studies of paresthesia injuries to oral surgery patients have determined that paresthesia is caused by a neurotoxicity of the local anesthetic. It is theoretically possible that, in those patients with an apparent "something" wrong with the structure of their ion channel, the normal conformational events in the ion pore can be precluded. There is a possible metabolic pathway for the breakdown of the local anesthetic molecule at the site of injection which would lead to the formation of an alcohol. In those patients with ion channel problems, the alcohol can remain "stuck" to the alpha helix of the ion channel, stabilizing it in its closed conformation and resulting in paresthesia (details in the enclosed papers). The use of alcohol with a higher incidence of oral carcinoma and other cancers has been studied.
8. The proposed chemistry of the paresthesia problem also results in the formation of oxygen and a free radical manufacturing mechanism.
9. There have been reports of the possibility of cancers resulting from pesticide use, and some pesticides specifically act on ion channels.
10. A metabolite of prilocane, ortho-toliudine, is carcinogenic in rats and mice, but such studies have not been done on lidocaine, dyclone, duranest, and polocaine.

In view of this association and relationship of the ion channel with cancers, it is contemplated as part of the invention, that one can identify the probability of pre-cancer or cancer condition using the method(s) of the invention, and the identification and assay of potential compositions to treat cancers. Also, one can treat cancers associated with dysfunction of sodium channels by use of non-carcinogenic lidocaine derivatives that have been rendered radiosensitive to ionizing radiation and subjecting a mammal or patient thus injected with the derivative with particle beam high energy radiation, or like means for activating the radiosensitive molecule attached to or associated with the lidocaine derivative.

EXAMPLE 6

Treatment of Cancer

In this example, a patient having melanoma cancer is treated using the methods of the present invention. A non-carcinogen form of lidocaine (e.g. the long chain residue of the molecule is modified to make it radiosensitive to ionizing radiation by methods known in the art). The modified lidocaine is then injected at or near the site of the tumors (although systemic injections may also be carried out). The patient is thereafter subjected to high energy radiation to activate the drug once it is in place in the ion channel. The radiation beam selectively destroys the cancer-associated dysfunctional channels where the lidocaine is targeted which leads to tumor resolution. The current ionizing radiation is conducted at a 40 angstrom definition of specificity. The lidocaine is specific only to 4 angstrom site of action which is the approximate size of the sodium channel of the thermal protein of the patient.

DISCUSSION:

I. AChE Preparation:

If the first 80,000 g spin was not quickly performed (see Table 1 and Table 2), loss of AChE to supernatant 1 would occur. Even placing the post-600 g fraction on ice did not prohibit the lysosomal-like digestion and a resultant loss of 10% AChE to supernatant I as occurred in Prep 8. These arguments are not completely for or against 0° C. digestion as a purification technique, but one must be aware of cryptic and latent properties when isolating an enzyme. Although empiricism might be a good method, rational approaches would probably give more complete information. (NH$_4$)$_2$SO$_4$ precipitation and cold room digestion were introduced into the preparation by empirical methodology.

Another problem requiring discussion is that protein determination profiles did not directly follow AChE activity profiles during column elution. Total nitrogen determinations of column samples agreed with the Lowry determinations. This observation becomes significant when the latest purification has a specific activity of 13,000 µM/mg/hr and has two components by disc acrylamide electrophoresis; yet the column elution pattern for this fraction did not have a protein profile corresponding to the activity profile. An interfering glycoprotein or lipid component may have been present in these fractions, preventing correspondence between the two profiles and acrylamide data.

II. Circular Dichroism

Circular dichroism was performed assuming that the AChE was soluble in buffer. Circular dichroisn can give physico-chemical information about a heterogeneous macromoleculels structure provided that molecule has an asymmetric grouping. Circular dichroism is an absorptive property of a molecule dependent on the chromophore's ability to absorb differentially the left and right circularly polarized components of plane-polarized light. Macromolecular analysis of polypeptide disulfide bridge, beta-pleated sheet, extended chain, and alpha helix in prototype proteins using CD can be done. Circular dichroism is useful in studying proteins in that the chromophore's effect is being measured in the region of its absorption band. AChE (eel) has been shown to have 7% tyrosine, 10% phenylalanine, 4% tryptophan and 2% cysteine, all of which can be distinguished by circular dichroism.

A Roussel-Jouan Dichrograph 11 sensitive to $1 \times 10^{-5}$ dichroic absorption units per recording mm was used with 10 mm strain-free quartz ORD cells. Circular dichroism was used to study the conformation of the mammalian AChE preparation macromolecule(s) in solution using established techniques and principles. The observed dichroism revealed a helical structure when compared to known helical dichroisms.

A curve showing the CD spectrum of AChE from 300 nm to 195 nm was made. Since CD is an absorptive 5 phenomenon occurring only at specific frequency intervals, the band at 222 nm has been attributed to a $n–\pi^*$ transition of the oxygen electrons of a peptide bond. At this wave-length, a minimum of random coil absorption occurred. Assuming polyglutamic acid to be 100% helix at 222 nm, AChE is calculated as having approximately 25% helix at 25° C.

Also a curve providing the information obtained by changing the temperature of the enzyme preparation over the range of 15° C. to 60° C. was made. This curve showed that the helical transition occurs in the temperature region near that of the bovine body temperature of 38.5° C. Helix is plotted against $|\Theta|$ at 222 nm. The helix-coil transition, which is reversible and endothermic, occurred between 30° C. and 40° C. The transition is labeled as a helix-coil transition because the curve indicates that the transition occurred with the formation of coil. However, the preparation still had considerable helix content even after the transition had occurred.

Simultaneous measurement of AChE activity gave a temperature dependent curve with a maximum of 37°–41° C. The helix-coil transition occurred without significant increase or decrease in enzyme activity.

In addition, enzyme activity was rapidly lost at 55° C. without a significant change in helix content. The helical content lost in the helix-coil transition was of the order of 40% based on maximum helical content of 25%. It appears that two steady states for helix conformation, which are independent of AChE activity, exist with a transition zone at 30°–40° C. One conformation exists from 15° C. to 30° C. and another from 40° C. to 60° C. It cannot be established from these data whether it is the AChE or some other molecular component in the preparation that exhibits the observed helix-coil transition.

Analysis of the helix-coil transition indicates that, unlike other helical melting curves that result in no helix after the transition, this preparation had helix remaining. The irreversibility of the transition may be explained by an incorrect refolding that does not permit a return to helical structure. Although pH studies using CD and AChE were not done, it has been found that addition of salts can stabilize a helix against changes in pH.

Table 9 presents the data for the effect of pilocarpine and lidocaine. Higher temperatures were necessary to elicit the helix-coil transition in the presence of these drugs. Pilocarpine had a positive ellipticity at 222 nm, and lidocaine had no ellipticity at 222 nm under the conditions used. The molar ellipticity $|\Theta|$ of the preparations in the presence of pilocarpine and lidocaine was minimally 5 times greater than the standard error for the helix-coil transition studies. It appears that only fresh AChE preparations can be stabilized by these drugs since the effect was not observed with enzyme preparations that were more than one week old.

III. Pharmacology

Hypotheses for the basis of anesthetic action have usually included a separation of central nervous system CCNS1 from peripheral nervous system (PNS1 mechanisms. It is difficult to establish a coherent relationship between physiological in vivo observation and physicochemical studies. However, these thermal studies of a helix-coil transition in an enzyme preparation known to be important in the control of neuronal excitability suggest a new experimental basis of a theoretical discussion of the properties of nerve transmission and anesthesia.

The molecular bases for a mechanism of general anesthesia (CNS) include physicochemical CNS theories such as the fat solubility hypothesis and the hydrated microcrystals or "iceberg" theory.

For anesthetic action in the peripheral nervous system, theories involving acetylcholinesterase's dual function as enzyme and receptor and a membrane-pore model have been suggested. The site of receptor function has been attributed to the neuron's postsynaptic membrane. By an unknown mechanism, arrival of a nerve impulse at a synapse (PNS) causes liberation of acetylcholine into the synaptic cleft. The transmitter crosses this space, and at those nerve junctions where acetylcholine is an excitatory neurohumoral agent, it acts on the postsynaptic membrane to increase the membrane's permeability to sodium and other small ions. Acetylcholinesterase is believed to end the action of acetylcholine by rapid hydrolysis. Acetylcholinesterase is found in high concentrations at the cell terminals which are cholinergic.

Acetylcholine, as a possible neurotransmitter, and acetylcholinesterase are present in muscle receptors, PNS ganglia and neuromuscular junctions. In the CNS, a large concentration of acetylcholinesterase is found in the caudate nucleus of the brain. Histochemical and pharmacological demonstrations of acetylcholine in the CNS suggested a neurohumoral role.

Local anesthetics are known to block the transient increase in permeability of neuron membranes to sodium ions and thus to prevent an action potential. Once the threshold for electrical excitability increases, blockage of neuronal conduction occurs. Perhaps the anesthetic acts at a receptor site that controls the permeability of the membrane as seen by the reduction of the resting membrane's permeability to sodium and potassium.

The PNS nerve transmission theories center around a 'pore' theory that permits an action potential provided a triggering agent like acetylcholine is present. The microcrystal theory (CNS) requires the disruption by changes in water structure of normal function of proteins or enzyme active centers necessary for the transmittance of neuronal impulses. The PNS and CNS may have a similar mode of nerve transduction at nerve terminals. The 'pore' theory may involve a macromolecule capable of changing shape to result in a membrane opening. In fact, recent molecular interpretations of receptor function have predicted the necessity of the receptor having the ability to undergo conformational changes. Should macromolecular changes occur, it is not difficult to recognize the importance of the structured environment about such a macromolecule. Understanding the cholinergic receptor, then, involves three factors: a neurotransmitter, a receptor on a nerve membrane, and the aqueous environment around that membrane receptor.

Certain properties of water have been suggested as important for the biological system and discontinuities in such water properties have been suggested for the temperatures 15°, 30°, 45° C., and 60° C. For example, in man and other mammals, loss of consciousness, which might be related to water structure, occurs below 30° C. Depression of the CNS by non-hydrogen bonding general anesthetics like cyclopropane, chloroform, nitrous oxide, halothane, and xenon have led to a theory based on the hydrated crystals in water.

Of special interest in the present context is the fact that Belleau has, in a theoretical argument, implicated water as the determinant of thermodynamic transitions in the interaction of the cholinergic muscarinic receptor and its counterparts. The model must account for physiologic responses that are completely opposite in nature, i.e. agonism versus antagonism. Using alkyl chains of different lengths, it was found that "dehydration" phenomenon of AChE would parallel the cholinomimetic potency of the drug molecules. Belleau states that "it is felt that this novel correlation between the effective displacement of a surface-bound water molecule and the pharmacological potency of a drug may have far-reaching implications in the field of molecular pharmacology." It is suggested that these perturbations of water structure at the receptor site might be due to the entropy-driven transfer of nonpolar solutes to the apolar site of a protein.

In the experimental work done using circular dichroism, the helix-coil transition begins at 30° C. It is an irreversible, endothermic reaction resulting in a more random state of the molecule(s). In crab and frog nerves, an "initial heat" or release of energy occurs with neuronal excitation. This initial, relatively large, production (580 ergs/gram-impulse) is followed by a somewhat smaller absorption of heat (500 ergs/gram-impulse). Perhaps, the observed helical transition may indeed be involved in "initial heat" and the endothermic follow-up. However, it is difficult to claim that the heat changes are due to a single molecular event.

The molecular action of both lidocaine and pilocarpine are not absolutely known. In terms of their CNS effects, both drugs are suspected to act through disinhibition to result in a common physiologic response of CNS stimulation. If their agonist effect is similar, one could predict a molecular event common to both as seen in the stabilization of the helix-coil transition in the CD studies.

The following receptor mechanism is proposed as one possible explanation for the observed data (see FIG. 18).

The helix-coil transition as elicited in the system studied did not result in total loss of helix, but instead in a partial loss of 40%. The specificity of this transition as well as its lack of any apparent relationship to AChE activity suggests the possibility of a functional molecular event. Should this be the case, the second helix conformation could represent a form of the molecule or a molecular group, at bovine in vivo temperatures, that permits neuronal ion influxes by opening pores with a resultant action potential.

Based on the observation that water may influence biologic actions at specific temperatures,it is possible that the helix-coil transition beginning at 30° C. is not coincidental. Belleau has suggested the importance of water structure in cholinergic receptors. The helix conformation from 15° C. to 30° C. may represent an inactive form of a functional molecule. Thus, it would not be surprising that unconsciousness in mammals would occur below 30° C. since an inactive form of the receptor molecule would exist at postsynaptic neuronal membranes. Perhaps agonist molecules disrupt the envelope of water around the helix.

Should a helix-coil transition be necessary for initiation of an action potential, drugs like pilocarpine and lidocaine may act to inhibit neuronal function by preventing such a transition. On the other hand, substances like acetylcholine might cause a helix-coil transition by disrupting the envelope of water around the helix. The receptor site, then, would represent an area of the functional molecule and not a site analogous to an enzyme's active site. It is an important point that an area or region consisting of a number of amino acid residues appears to be involved in the helical changes seen with circular dichroism. Since the helix-coil transition is irreversible in the present system, it is possible that a structured environment necessary for the receptor to return to its inactive form is missing in the system studied.

The effect of lyophilization on CD may represent a dehydration effect. It has been shown that in fibrillar collagen proteins, water has a very important structural function. If hydration is important for collagen structure, dehydration has resulted in severe disordering. Interestingly, the AChE preparation shows a sudden loss of helix and AChE activity with a concurrent increase in coil. Perhaps the loss of water is an important determinant of the helix in this preparation while the AChE active site might exist in an area represented by the increase in coil.

The effect of $MgSO_4$ salts on an AChE preparation was unexpected. Although one cannot attribute an effect specifically to either the $Mg^{++}$ or $SO_4^{++}$ ions, it would be interesting to decipher the meaning of loss of helix with the masking of AChE activity (Table 5). Perhaps the AChE activity is not related to changes in helical content.

Circular dichroism using a Jouan Dichrograph 11 was undertaken to study a partially purified thermal proteins acetylcholinesterase ("AChE"), isolated from caudate nucleus of bovine brain. A helix absorption (CD) was observed for the AChE preparation at a minimum of 222 nm through a spectral range of 300 nm to 185 nm using $N_2$ purge. On variation of temperatures by 50° C. intervals from 15° C. to 60° C., the helix went from one distinct conformation to a second helical conformation between the temperatures 30° C. and 40° C. with a 40% loss of helix content. The temperature activity optimum of the AChE was 37°–41° C., which is close to the bovine body temperature of 38.5° C.

It is known that a helix will seek the minimum energy state in water and that some functional proteins go through remarkable rate changes between 30° C. and 40° C. The helical transition observed represented a change of the helix to a more random state. Further studies indicated the helical transition was probably independent of enzyme activity. Since this was the case, it is possible that the transition is a function of a macromolecule that may have "receptor" properties. Macromolecules capable of conformational changes have been proposed by many groups as drug "receptors", but never demonstrated in vitro as isolated substances. Tests of such a hypothesis include examination of the influence of pharmacological agents on the conformation of the protein(s). In preliminary studies pilocarpine and lidocaine prevent the helical transition observed between 30° C. and 35° C.

A model for a receptor mechanism and of anesthetic action was suggested which could possibly be applied to both central and peripheral nervous systems. The mechanism of neuronal transmission was suggested to be a helix capable of uncoiling and recoiling to open pores in the postsynaptic membrane to permit neuronal stimulation by ion influxes. Anesthesia could be easily obtained provided the drug served to prevent the helical area from undergoing structural changes by possibly interferring in helix hydration structure. On the other hand, other molecules may cause a disruption in the envelope of water around the helix to result in uncoiling. The stabilization might be preferably accomplished by non-covalent helix/drug interactions to permit reversibility of the drug action under in vivo conditions.

PHARMACOLOGY OF LOCAL ANESTHETICS

Local anesthetic agents are classified according to their duration of activity as short-, moderate-, and long-acting drugs. Their chemical structure is classified as an ester or an amide.

DURATION OF EFFECTIVE ACTION

As with all drugs, local anesthetic agents follow the known rules pertaining to pharmacologic action. In particular, they follow the expected bell-shaped curve in relation to duration of action, in that the drug is not effective for a few patients, is successful for the vast majority, and has a long duration, to the point of permanency, in a few patients.

Short-acting local anesthetics (1–2 hours) include procaine and lidocaine. Procaine, an ester, is usually hydrolyzed in the plasma by an esterase to end its action. Lidocaine, an amide, is degraded in the liver. Lidocaine produces fewer known allergic reactions than procaine.

Moderate-acting local anesthetics (2–3 hours) include lidocaine with epinephrine, mepivacaine, and prilocaine. Adding epinephrine, which produces vasoconstriction, to lidocaine prolongs the duration of action, which may be advantageous for most patients. However, if cardiac sensitization to the catecholamine is a possibility, the dosage must be adjusted for cardiac patients. A side effect of both lidocaine and prilocaine is drowsiness. A side effect of prilocaine in doses greater than 400 mg has been methemoglobinemia. Mepivacaine has a rapid onset. A unique synergistic property of prilocaine and mepivacaine produces a more profound regional anesthesia than when either is administered alone.

Long-acting anesthetic agents (4–18 hours) include bupivacaine and etidocaine with and without epinephrine.

PHYSIOLOGIC EVENTS OF LOCAL ANESTHETIC PHARMACOLOGY

Local anesthetic agents stabilize neural membranes by inhibiting the ionic fluxes required for the propagation of neural impulses. The resultant anesthetic action initially affects the pain fibers first; the pain fibers are the least myelinated and are the smallest of the nerve fibers. Then, in a progressive manner unique to this family of drugs, the action moves on to the larger and more myelinated fibers. The patient experiences the successive loss of the sensations of pain, cold, warmth, touch, pressure, proprioception, and, finally, motor function.

The property of local anesthetics to selectively block action of the pain fibers permits somatically painless surgery. If, owing to the bell-shaped curve of drug action, the local anesthetic agent does not affect the pressure and touch fibers, then general anesthesia or sedation may be indicated.

Mechanism of Action of Local Anesthetics

The site of local anesthetic molecular action is the sodium channel membrane pore, which permits ion influx. This neuroreceptor site in the pore must have the ability to undergo conformational change from a closed to an open configuration and yet be blocked by local anesthetics to prevent the action potential of nerve propagation.

Noda et al reported a sodium channel neuroreceptor from DNA sequencing (Noda, M., Shimizu, S., Tanabe, T., et al.: Primary structure of electrophorus electricus sodium channel deduced from cDNA sequence. Nature 312:121–134, 1984). This study described the receptor as an alpha-helical structure with a molecular weight of 200,000 with differing numbers of subunits. Additionally, these researchers noted that the pKa of the sodium channel neuroreceptor is altered by changes in its DNA genome. In the human CNS, these alpha-helical proteins are associated structurally with the hydrolyzing enzyme acetylcholinesterase. Butterworth and Strichartz (Butterworth, J. F., Strichartz, G. R.: Molecular mechanisms of local anesthetics: A review. *Anesthesiology* 72:711–734, 1990) theorized that the actual nature of the sodium channel is a helical protein pore capable of opening and closing. It is suggested that three or four pairs of helical segments constitute each pore and behave as an electrical dipole. When the membrane is depolarized, these dipoles shift locally to allow helical uncoiling and resultant opening of the pore. Local anesthetics bind with the helices on the inner surface of the neuromembrane to inhibit the helical rearrangement and consequently result in anesthesia.

This biochemical understanding of the sodium channel structure, function, ionization, and enzyme association has valuable clinical application for the clinician in dentoalveolar surgery.

Metabolism of Local Anesthetics

The fate of local anesthetics depends on their biotransformation through systemic degradation, plasma hydrolysis, and local intracellular metabolism. The breakdown products of the local anesthetic are balanced against drug action in the host. The ester group of local anesthetics (procaine and tetracaine) undergo hydrolysis in the serum by plasma cholinesterase and liver esterases. The amide group of local anesthetics is metabolized in the liver through N-dealkylation and subsequent hydrolysis and excreted through the kidneys. The rate of degradation can be influenced by pre-existing host disease of the liver or kidney.

An increase in local metabolic rate (as may occur during third molar surgery or other surgical procedures) can result in the hydrolysis of both ester and amide anesthetics intracellularly at the site of injection; their hydrolysis probably is mediated by the channel-associated acetylcholinesterase. The increased local metabolic rate increases the demand for oxygen. Hydrolysis of the local anesthetic molecule can result in an alcohol and the needed oxygen. The degradation product for an ester molecule is two long-chain alcohols and a reactive oxygen. In theory, the amide group of local anesthetics is reduced by enzymatic hydrolysis to one long-chain alcohol, a reactive aromatic amine, and reactive oxygen. Paresthesia may result from the administration of a local anesthetic followed by its localized hydrolysis and production of an alcohol byproduct in a membrane's sodium channel. The metabolic chemistry of local ion channel events may explain Gruber's observation that ester local anesthetics cause more paresthesia than amide local anesthetics, 12 because the metabolism of the ester results in the production of twice as many alcoholic molecules as the metabolism of the amide.

Anesthesia Model

The neuroreceptor of the neuromembrane sodium channel is the site of activity of local anesthetics, sedative hypnotics (alcohol, barbiturates), neuroleptics, steroids, and aspirin (salicylic acid) derivatives. Because of its importance, considerable effort has been expended to understand the structure and function of the neuroreceptor of the neural membrane sodium channel.

Figure 3:
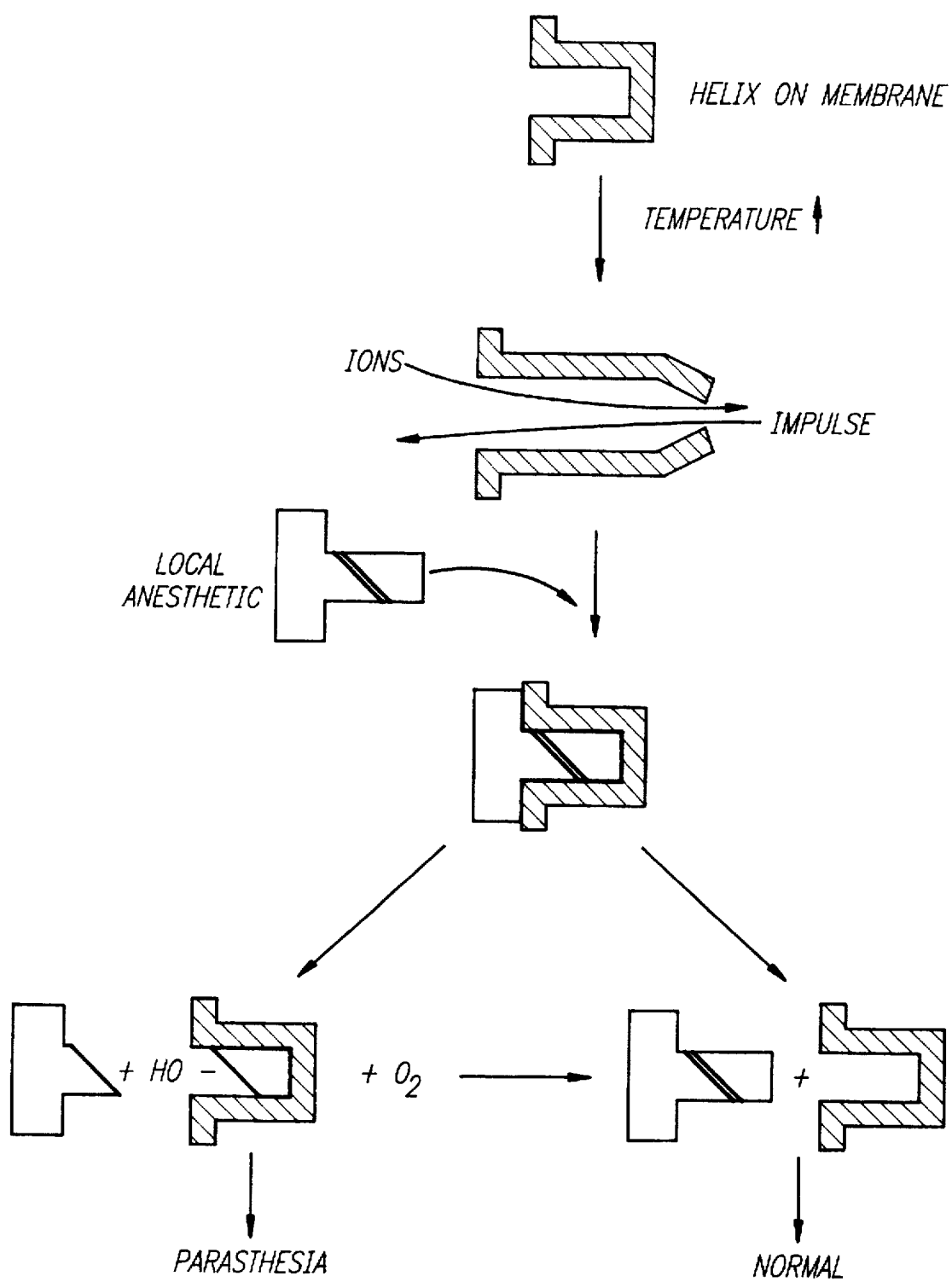
FIG. 3 is a model of anesthesia showing a receptor "pore" that opens when, in response to a localized increase in termperature, the alpha-helix partially uncoils, allowing an influx of ions and thus the propagation of nerve action potential.

A model of anesthesia is shown in FIG. 3 where a receptor "pore" that opens when, in response to a localized increase in temperature, the alpha-helix partially uncoils, allowing an influx of ions and thus the propagation of nerve action potential. The local anesthetic locks onto the coiled alpha-helix, preventing its uncoiling and thus also preventing the ion influx and nerve transmission of an action potential, e.g., pain.

If the local anesthetic molecule is hydrolyzed while still bound to the alpha-helix, an alcohol product can persist at the sodium channel pore. An intraneuronal metabolite like alcohol interferes with nerve conduction. Under exceptional conditions, lidocaine can produce an alcohol to give nerve dysfunction-like paresthesia.

A study using a purified bovine acetylcholinesterase preparation identified an alpha-helical protein that is thermodependent for structural uncoiling from one stable form to a second, less coiled stable form. The thermodependence appears to relate to initial intracellular heat production prior to an action potential propagation. This endothermic reaction results in the more random state of the alpha-helix. The initial heat produced prior to nerve impulse propagation may fulfill the mechanical requirement for energy by the channel pore receptor for its function and may explain why heat must be used in vitro to observe the structural change of the alpha-helix (gate theory of anesthesia). As observed using circular dichroism, the addition of the local anesthetic lidocaine to the preparation prevented this partial uncoiling of the alpha-helix, stabilizing it in its "closed" conformation despite increased temperatures as shown in the data in the tables and FIG. 2. Thus, this alpha-helical heat-activated protein in the membrane channel can explain the pore theory of ion influx, nerve impulse propagation, and anesthesia; but the key to understanding the structure and function of the neuroreceptor itself is the clinical and laboratory properties of the local anesthetic.

New Concepts of Local Anesthetic Theories

It is now plausible that channel structure is four amphipathic alpha-helices of a protein macromolecule, and dysfunction of the structure leads to such disease states as cardiac arrhythmia, angina pectoris, cystic fibrosis, and myotonia. Theories in general anesthesia have been based on the membrane lipid; but after 20 years of looking for factual supporting evidence, biophysicists are now looking at the ion channel as the protein receptor. The intraneuronal metabolic chemistry of local anesthetic neurotoxicity (the result of the hydrolysis of the local anesthetic to an alcohol) led to the confirmation of an alpha helical protein associated with a hydrolyzing enzyme as the operating molecule of the sodium channel for normal transmission and as the site of local anesthetic action. Study of this molecular structure and its function may lead to a more fundamental understanding of many disease processes, e.g., pain, epilepsy, allergy, alcoholism, and tumor formation. For example, neuropeptides are secreted through the neuromembrane pores during allergic reactions. This may be the molecular event that precepitates anaphylactic reaction by a dysfunction of the sodium channel pore's helical protein, the basic controlling modulator of neuroimmunology. A similar neuropeptide release is involved in ovarian carcinoma, which raises questions concerning sodium-channel modulator dysfunction as a primary factor in tumor growth. Events of anaerobic metabolism may then explain carcinogenesis by producing a free radical oxygen.

The present invention provides an unique membrane isolation and purification procedure that can preserve the sodium channel in a suitable status for circular dichroism.

The invention now being fully described, it will be apparent to one of ordinary skill in the art that many changes and modifications can be made thereto without departing from the spirit or scope of the invention as set forth herein.

I claim:

1. A method for determining abnormality in the structural conformation of a sodium channel thermal protein comprising the steps of:
   (a) forming a mixture of a test sodium channel thermal protein and a molecule capable of blocking or preventing the normal function of the sodium channel thermal protein in an excitable cell,
   (b) subjecting the mixture to circular dichroism at a wave length of 222 nM wave length measuring the transition of molar ellipticity while varying the temperature of said mixture between 25°–50° C., and
   (c) comparing said transition with the transition of molar ellipticity of a control normal sodium channel protein to ascertain the difference in structural conformation of the test sodium channel protein.

2. The method of claim 1 wherein the molecule is selected from the group consisting of lidocaine, derivatives of lidocaine, pilocarpine, and brevetoxin.

3. The method of claim 1 wherein the molecule has a binding site on sodium channels and said binding site is directly or indirectly linked with the binding site of lidocaine; said molecule being selected from the group consisting of: (a) tetrodotoxin and its derivatives that are capable of blocking the sodium currents; (b) batrachotoxin, veratridine and their lipophilic derivatives and analogs that are capable of activating sodium channels; (c) α-, or β-scorpion toxins, sea anemone polypeptide neurotoxins and their respective derivatives that are capable of prolonging the open status of sodium channels; and (d) DDT and synthetic pyrechroid insecticides and their analogs that are capable of activating sodium channels.

4. The method of claim 1 wherein the protein is obtained from the excitable tissues derived from a mammal with a disease selected from the group consisting of CNS diseases, cardiac disease, peripheral nervous system disease and tumor.

5. The method of claim 4 wherein the diseases are cardiac arrhythmias, angina rectoris, cystic fibrosis, myotonia or epilepsies.

6. The method of claim 1 wherein the temperature of the mixture is between 30°–35° C. and the molecule is selected from the group recited in claim 2.

7. A method for determining when a test compound affects the conformation of a sodium channel in a manner similar to a compound which is capable of blocking or impairing the sodium channel, comprising:

(a) forming a mixture of a sodium channel protein and the test compound.

(b) subjecting the mixture to circular dichroism at a wave length of 222 nM wave length measuring the transition of molar ellipticity while varying the temperature of said mixture between 25°–50° C., and (c) comparing said transition with the transition of molar ellipticity of (i) a control sodium channel protein alone and (ii) a mixture of the sodium channel protein and a compound capable of blocking or preventing the normal function of the sodium channel in an excitable cell.

8. The method of claim 7 wherein the molecule is selected from the group consisting of lidocaine, and derivatives of lidocaine.

9. The method of claim 7 wherein the molecule has a binding site on sodium channels and said binding site is directly or indirectly linked with the binding site of lidocaine; said molecule being selected from the group consisting of: (a) tetrodotoxin and its derivatives that are capable of blocking the sodium currents; (b) batrachotoxin, veratridine and their lipophilic derivatives and analogs that are capable of activating sodium channels; (c) $\alpha$-, or $\beta$-scorpion toxins, sea anemone polypeptide neurotoxins and their respective derivatives that are capable of prolonging the open status of sodium channels; and (d) DDT and synthetic pyrechroid insecticides and their analogs that are capable of activating sodium channels.

10. The method of claim 7 wherein the temperature of the mixture is between 30°–35° C. and the molecule is selected from the group recited in claim 2.

* * * * *